US011268109B2

(12) United States Patent
Shen et al.

(10) Patent No.: US 11,268,109 B2
(45) Date of Patent: *Mar. 8, 2022

(54) CHO INTEGRATION SITES AND USES THEREOF

(71) Applicant: REGENERON PHARMACEUTICALS, INC., Tarrytown, NY (US)

(72) Inventors: Ying Shen, Yorktown Heights, NY (US); Darya Burakov, Tarrytown, NY (US); Gang Chen, Yorktown Heights, NY (US); James P. Fandl, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/175,025

(22) Filed: Feb. 12, 2021

(65) Prior Publication Data

US 2021/0171984 A1 Jun. 10, 2021

Related U.S. Application Data

(63) Continuation of application No. 16/575,506, filed on Sep. 19, 2019, which is a continuation of application No. 15/783,525, filed on Oct. 13, 2017, now abandoned, which is a continuation of application No. 14/919,300, filed on Oct. 21, 2015, now Pat. No. 8,916,110.

(60) Provisional application No. 62/067,774, filed on Oct. 23, 2014.

(51) Int. Cl.
*C12N 15/113* (2010.01)
*C12N 15/90* (2006.01)
*C12N 15/85* (2006.01)

(52) U.S. Cl.
CPC .......... *C12N 15/907* (2013.01); *C12N 15/85* (2013.01)

(58) Field of Classification Search
CPC .... C12N 15/113; C12N 15/63; C12N 510/00; C12N 51/0682
See application file for complete search history.

(56) References Cited

U.S. PATENT DOCUMENTS

| 6,689,606 | B2 | 2/2004 | Antoniou et al. |
| 7,771,997 | B2 | 8/2010 | Chen et al. |
| 8,389,239 | B2 | 3/2013 | Chen et al. |
| 8,673,589 | B2 | 3/2014 | Chen et al. |
| 9,816,110 | B2 | 11/2017 | Shen et al. |
| 2004/0137572 | A1 | 7/2004 | Finney et al. |
| 2013/0122591 | A1 | 5/2013 | Cost et al. |
| 2013/0326645 | A1 | 12/2013 | Cost et al. |
| 2014/0179005 | A1 | 6/2014 | Jantz et al. |
| 2016/0115502 | A1 | 4/2016 | Shen et al. |
| 2018/0030480 | A1 | 2/2018 | Shen et al. |
| 2020/0002732 | A1 | 1/2020 | Shen et al. |

FOREIGN PATENT DOCUMENTS

| CN | 102625655 A | 8/2012 |
| JP | 2002-526071 A | 8/2002 |
| WO | 02/081632 A2 | 10/2002 |
| WO | 2008/151219 A1 | 12/2008 |
| WO | 2012/138887 A1 | 10/2012 |
| WO | 2012/145493 A1 | 10/2012 |

OTHER PUBLICATIONS

Aldrich T.L. et al., "EASE Vectors for Rapid Stable Expression of Recombinant Antibodies", Biotechnol. Prog. 19:1433-1438 (2003).
Araki K. et al., "Site-Directed Integration of the Cre Gene Mediated by Cre Recombinase Using a Combination of Mutant Lox Sites", Nucleic Acids Research 30(19):e103 (2002).
Bahr S. et al., "Evaluating the Effect of Chromosomal Context on Zinc Finger Nuclease Efficiency", BMC Proceedings 7(Suppl 6):P3 (Dec. 4, 2013).
Boch J. et al., "Breaking the Code of DNA Binding Specificity of TAL-Type III Effectors", Science 326:1509-1512 (Dec. 11, 2009).
Bouhassira E.E. et al., "Transcriptional Behaviour of LCR Enhancer Elements Integrated at the Same Chromosomal Locus by Recombinase-Mediated Cassette Exchange", Blood 90(9):3332-3344 (Nov. 1, 1997).
Chen H. et al., "Cut Site Selection by the Two Nuclease Domains of the Cas9 RNA-Guided Endonuclease", The Journal of Biological Chemistry 289(19):13284-13294 (May 9, 2014).
Fisher S. et al., "A Scalable, Fully Automated Process for Construction of Sequence-Ready Human Exome Targeted Capture Libraries", Genome Biology 12:R1 (2011).
Fukushige S. et al., "Genomic Targeting With a Positive-Selection Lox Integration Vector Allows Highly Reproducible Gene Expression in Mammalian Cells", Proc. Natl. Acad. Sci. USA 89:7905-7909 (Sep. 1992).
Kent W.J., "BLAT—The BLAST-Like Alignment Tool", Genome Research 12(4):656-664 (2002).
Kito M. et al., "Construction of Engineered CHO Strains for High-Level Production of Recombinant Proteins", App Microbiol Biotechnol 60:442-448 (2002).
Koduri R.K. et al., "An Efficient Homologous Recombination Vector pTV(I) Contains a Hot Spot for Increased Recombinant Protein Expression in Chinese Hamster Ovary Cells", Gene 280:87-95 (2001).

(Continued)

*Primary Examiner* — Karen Cochrane Carlson
(74) *Attorney, Agent, or Firm* — Scully, Scott, Murphy & Presser, P.C.; Todd R. Samelman

(57) ABSTRACT

Expression-enhancing nucleotide sequences for eukaryotic expressions systems are provided that allow for enhanced and stable expression of recombinant proteins in eukaryotic cells. Genomic integration sites providing enhanced expression and methods of use thereof are provided for expression of a gene of interest in a eukaryotic cell. Chromosomal loci, sequences, and vectors are provided for enhanced and stable expression of genes in eukaryotic cells.

15 Claims, 4 Drawing Sheets

Specification includes a Sequence Listing.

(56) References Cited

OTHER PUBLICATIONS

Kwaks T.H.J. et al., "Employing Epigenetics to Augment the Expression of Therapeutic Proteins in Mammalian Cells", TRENDS in Biotechnology 24(3):137-142 (Mar. 2006).
Lattenmayer C. et al., "Identification of Transgene Integration Loci of Different Highly Expressing Recombinant CHO Cell Lines by FISH", Cytotechnology 51(3):171-182 (Nov. 15, 2006).
Lewis N E et al., "Genomic Landscapes of Chinese Hamster Ovary Cells Lines as Revealed by the Cricetulus Griseus Draft Genome", Nature Biotechnology 31(8):759-765+2PP (Aug. 2013).
Li Q. et al., "Locus Control Regions", Blood 100(9):3077-3086 (Nov. 1, 2002).
Mayrhofer P. et al., "Accurate Comparison of Antibody Expression Levels by Reproducible Transgene Targeting in Engineered Recombination-Competent CHO Cells", Appl Microbiol Biotechnol 98:9723-9733 (2014).
Mielke C. et al., "Anatomy of Highly Expressing Chromosomal Sites Targeted by Retroviral Vectors", Biochemistry 35:2239-2252 (1996).
Sadelain M. et al., "Safe Harbours for the Integration of New DNA in the Human Genome", Nature Reviews—Cancer 12(1):51-58 (Jan. 1, 2012).
Shmerling D. et al., "Strong and Ubiquitous Expression of Transgenes Targeted into the B-Actin Locus by Cre/Lox Cassette Replacement", Genesis 42:229-235 (2005).
Stella S. et al., "BuD, a Helix-Loop-Helix DNA-Binding Domain for Genome Modification", Acta Crystallographica D70:2042-2052 (2014).
Svetlova E.Y. et al., "Mammalian Recombination Hot Spot in a DNA Loop Anchorage Region: a Model for the Study of Common Fragile Sites", Journal of Cellular Biochemistry Supplement 36:170-178 (2001).
Turan S. et al., "Site-Specific Recombinases: From Tag-and-Target-to Tag-and-Exchange-Based Genomic Modifications", The FASEB Journal 25:4088-4107 (2011).
Xu X. et al., "The Genomic Sequence of the Chinese Hamster Ovary (CHO)-K1 Cell Line", Nature Biotechnology 29(8):735-741 (Aug. 2011).
Zhou H. et al., "Generation of Stable Cell Lines by Site-Specific Integration of Transgenes into Engineered Chinese Hamster Ovary Strains Using an FLP-FRT System", Journal of Biotechnology 147(2):122-129 (May 17, 2010).
Gen-Bank Locus ID No. AFTD01150902.1, nt35529:39558 (2011) (15 pages total).
International Search Report and Written Opinion dated Mar. 21, 2016 received in International Application No. PCT/US2015/056653.
Chinese Office Action dated Mar. 9, 2020 received in Chinese Patent Application No. 201580069889.1, together with an English-language translation.
English-language Translation of Taiwanese Search Report dated Feb. 21, 2020 received in Taiwanese (ROC) Patent Application No. 104134716.
Japanese Notice of Reasons for Rejection dated Sep. 6, 2019 received in Japanese Patent Application No. 2017-519646, together with an English-language translation.

Figure 1A. Integration at SEQ ID NO:1 locus:
Figure 1B. Flourescent marker donor vector:
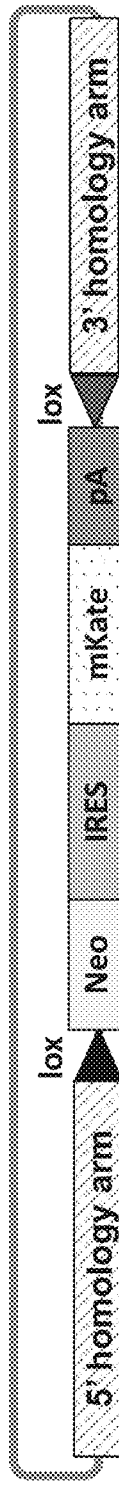

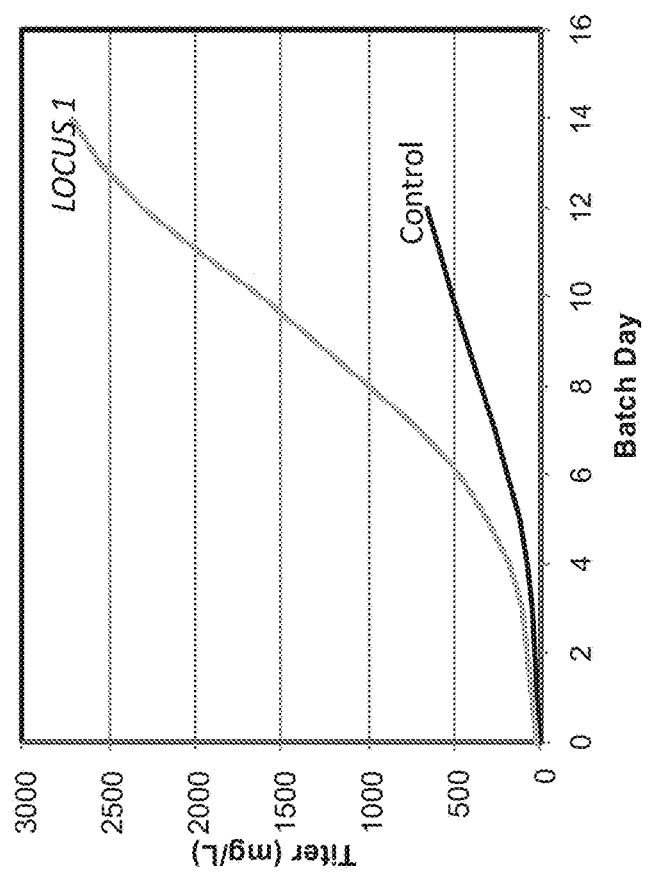
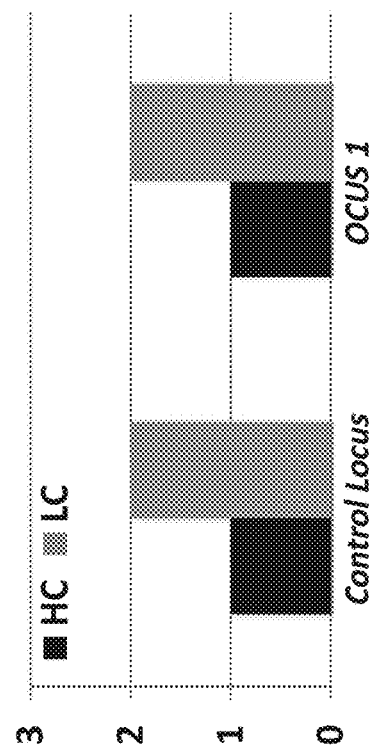
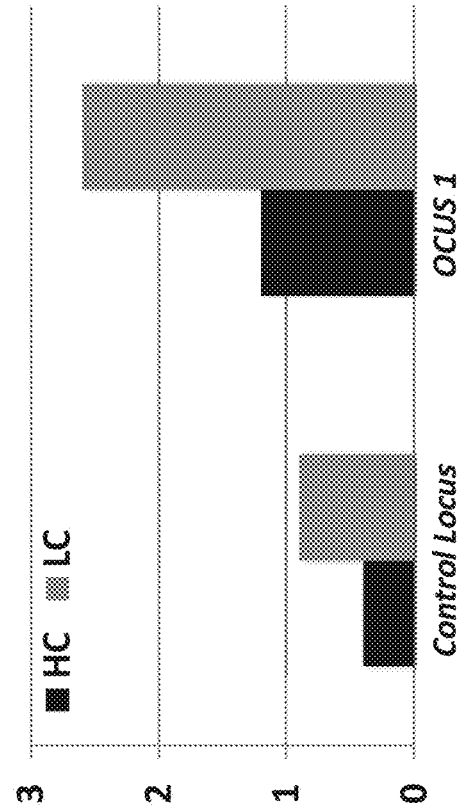

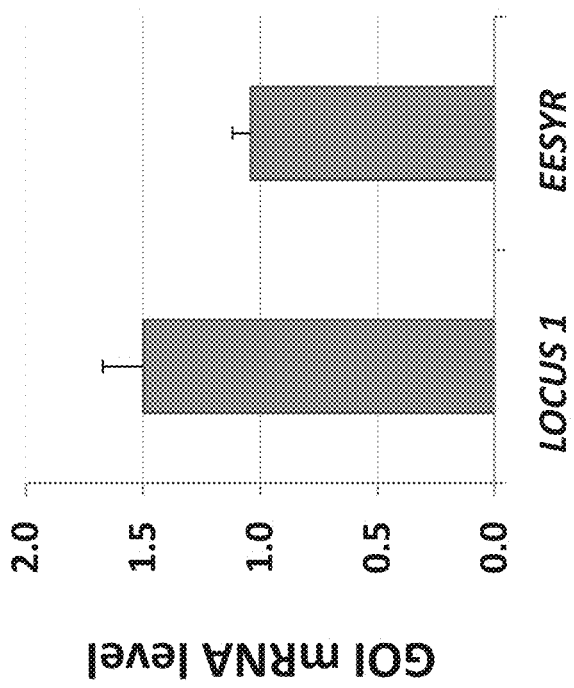
Figure 4. Engineered LOCUS 1 supports RMCE and high-level transcription

SEQUENCE LISTING

```
<160> NUMBER OF SEQ ID NOS: 6

<210> SEQ ID NO 1
<211> LENGTH: 4001
<212> TYPE: DNA
<213> ORGANISM: Cricetulus griseus

<400> SEQUENCE: 1
ccaagatgcc catcaactga ttaatagatg ataaaattat tgtacatttc agtgtaatat        60
tattcagttt ttaagaaaaa tgaaattatg taataagcat gtaaatggat atatcttgaa       120
acaaccattc cccattatat tacctaaaca ttgaaagtcc aaaatcatat gatcttttta       180
gtggatctac taatcttttg ctatatgtat tttattgaac tacccatgga tgtgagataa       240
ttggtaacaa cagcacatgg gagagcatgg gatcattcaa ggaagattag agagaatgca       300
ttttttagga gataatggag gagcaataga aaggattaaa tgaggttact gatgaaagtg       360
atggttagag aaggcaatat gaggagggat aactagcact tagggccttt tgaaaaagac       420
atagagaaaa tactattgta gaaacttcct ataattggtg tatagttata tacaccaaag       480
agctcagatg gagttaccct ataatggaaa tattaactac tttttatcac tgtgataaaa       540
catcctgaac agagcaacat agattgggaa gcatttactt tggcttacag ttctaacggg       600
ataaaaattc atgatgaaag aatgaatatg tcagcaaaca gcagtagcaa tggcctgaga       660
agcaggtgag agctcacatc ttgaagtgta agaatgtagc agagagaaca aactgcaaat       720
gaccagaaaa tgcttttgga tcagagccca tacccctctg actgacttct ccagaaattc       780
tgaacaaata aaactcccca aacagagcca taactgaagg tccagtgtct gagactacta       840
ggggtatttc ttattcaaac cactacaatg gggtggggggg agcaatcctc caagtaggca       900
ctacacacag acaaataaaa actctagtaa ctggaatgga ttgacttatt tgaattactt       960
```

-continued

```
gccagtggag ctacatagag cacaattatt gtatttaaat tacccttat gatcttacaa      1020 aacttgacag taagatcata ttgctaaaga aaccacatat ttgaatcagg aacatggtg      1080 atatctagtt gttcttcaac tggaaacttc atgctttctg cccagcattc atgttgctgg      1140
aaagagcaat gtacactacc agtgtagaaa ttaaatcatc aatcttatca agatgtggat      1200
cctataagtt acaataaaaa ttagcctgat aagatatccc caccagaaga atattcacat      1260
aaatgctatg ggagcaacaa gctattttct aaattagctt taatcctatt ctacaagaga      1320
gaatccatat ctagaatagt tatagggatc aagaacccat ggcttgattg gtcataggcc      1380
caatgggaga tcctaatatt attgttctac aaaatgaaaa taactcctaa tgacttgttg      1440
ctgcagtaat aagttagtat gttgctcaac tctcacaaga gaagttttgt cttacaataa      1500
atggcaatta aagcagcccc acaagattta tatcataccg atctcctcat ggcctatgca      1560
tctagaagct aggaaacaaa gaggaccta agagagacat acatggtccc cctggagaag      1620 ggaaggggg caagacctcc aaagctaatt gggagcatgg gggaggggag agggagttag      1680
aagaaagaga agggataaa aggagggaga ggaggacaag agagagaagg aagatctagt      1740
caagagaaga tagaggagag caagaaaaga gataccatag tagagggagc cttgtatgtt      1800
taaatagaaa actggcacta gggaattgtc caaagatcca caaggtccaa ctaataatct      1860
aagcaatagt cgagaggcta ccttaaaagc ctttctctga taatgagatt gatgactacc      1920
ttatatacca tcctagagcc ttcatccagt agctgatgga agcagaagca gacatctaca      1980
gctaaacact gagctagttg cagacaggga ggagtgatga gcaaagtcaa gaccaggctg      2040
gagaaacaca cagaaacagc agacctgaaa aaaatgttgc acatggaccc cagactgata      2100
gctgggagtc cagcatagga ctttctaga aaccctgaat gaggatatca gtttggaggt      2160
ctggttaatc tatggggaca ctggtagtgg atcaatattt atccctagtt catgactgga      2220
atttgggtac ccattccaca tggaggaatt ctctgtcagc ctagacacat gggggaggtt      2280
ctaggtcctg ctccaaataa tgtgttagac tttgaagaac tcccttgaga agactcaccc      2340
tccctgggga gcagaaaggg gatgggatga gggttggtga gggacaggag aggaggggag      2400
ggtgagggaa ctgggattga caagtaaatg atgcttgttt ctaatttaaa tgaataaagg      2460
aaaagtaaaa gaagaaaaga aaacaggcca aaagattata aagacagag gtggtgggtg      2520 actataaaga aacactatta tctaaataaa aacatgtcag aagcacacat gaacttatag      2580
tgtttatgaa agtatgtata ataactacat aatctcaagc caagaaaaaa atatcatctt      2640
tcagtgatga aggtgatttt attctctccca gaattaaagc caaagaccta atgaaagtaa      2700
ttatcttcaa aaggttgaaa atacatactt tgcaatacac agatctgcct agaaatctca      2760
tgttcacaat acacatgatg ctcaattgaa ttccattcaa tgttacagtt tagataaaca      2820
gtttgtagat aaactcacaa tgtatcattt cttttatt tttgaccaaa cagcttctca      2880
tctgttattc agaataattc ctcgatggca ggatatccat cccaattggg ggaaggggag      2940
aatttgaaga aaacctagac cacatacata tttgccattg ggaaacaaag tctaaaatga      3000
tgttgttcac atcttctcta ctagtcctct ccccgtccca agaaccttg gtatatgtgc      3060 ctcattttac agagagagga aagcaggaac tgagcatccc ttacttgcca tcctcaaccc      3120
aaaatttgca tcattgctca gctctgccct tctcatatga cagttacaag tcaaggcttc      3180
caaagtccct ctgtcatgtt tggtgtcaat agtttataca gatgacttca tgtcttcata      3240
tctaatgtct tatatagatt aatattaaac aatgttattt ctctaaccac attttaaatt      3300 aattaaaaa tccattaatt gtgtctataa aatgcagaca gagtgctgag acacaatata      3360
```

| | |
|---|---|
| agcctgatga tctgaatttg aaactcacac ccaccacatg gagaatcaac ttccaaaaat | 3420 |
| tttcctatta cttccacact tacaccattg tacaaacaca ataataatga acaaaatgaa | 3480 |
| atgaaataaa aaattaagtc tctgtaggta atgctactgt gcagcaaaag taaaaatggc | 3540 |
| agcttaagct tgctttatgg ttacacttta ccatcttcca ttaattataa ggacttcaat | 3600 |
| catggcagaa ctatgctgtt attgtctcag tgtaacctaa ccaggtgttc cagatgttct | 3660 |
| taatgtggac acctaaacta tttgatattt gggttaagat ctttccctct ttcagaagaa | 3720 |
| acctcaggac agagggaatc ttgtctttta attttgagtc tgtagacttt ttccatttca | 3780 |
| aatatacatg aaacaagtga tgaagaaaat taatcaaaag gtgggaattg caatgatatt | 3840 |
| aggttcaata ttaagcttca atattatcat ggaatcgcct gttatacact gagtgtttgg | 3900 |
| caataaggga tttttagaag aaggagtttt tattctcaac aggttcctta agtttagctc | 3960 |
| aaataaatct aagcaatcca ctctagaatt aaatagtttc c | 4001 |

<210> SEQ ID NO 2
<211> LENGTH: 1001
<212> TYPE: DNA
<213> ORGANISM: Artificial Sequence
<220> FEATURE:
<223> OTHER INFORMATION: synthetic polynucleotide

<400> SEQUENCE: 2

| | |
|---|---|
| tacccttat gatcttacaa aacttgacag taagatcata ttgctaaaga aaccacatat | 60 |
| ttgaatcagg gaacatggtg atatctagtt gttcttcaac tggaaacttc atgctttctg | 120 |
| cccagcattc atgttgctgg aaagagcaat gtacactacc agtgtagaaa ttaaatcatc | 180 |
| aatcttatca agatgtggat cctataagtt acaataaaaa ttagcctgat aagatatccc | 240 |
| caccagaaga atattcacat aaatgctatg ggagcaacaa gctattttct aaattagctt | 300 |
| taatcctatt ctacaagaga gaatccatat ctagaatagt tatagggatc aagaacccat | 360 |
| ggcttgattg gtcataggcc caatgggaga tcctaatatt attgttctac aaaatgaaaa | 420 |
| taactcctaa tgacttgttg ctgcagtaat aagttagtat gttgctcaac tctcacaaga | 480 |
| gaagttttgt cttacaataa atggcaatta aagcagcccc acaagattta tatcataccg | 540 |
| atctcctcat ggcctatgca tctagaagct aggaaacaaa gaggaccctt agagagacat | 600 |
| acatggtccc cctggagaag gggaaggggg caagacctcc aaagctaatt gggagcatgg | 660 |
| gggagggga gggagttag aagaaagaga aggggataaa aggagggaga ggaggacaag | 720 |
| agagagaagg aagatctagt caagagaaga tagaggagag caagaaaaga gataccatag | 780 |
| tagagggagc cttgtatgtt taaatagaaa actggcacta gggaattgtc caaagatcca | 840 |
| caaggtccaa ctaataatct aagcaatagt cgagaggcta ccttaaaagc ctttctctga | 900 |
| taatgagatt gatgactacc ttatatacca tcctagagcc ttcatccagt agctgatgga | 960 |
| agcagaagca gacatctaca gctaaacact gagctagttg c | 1001 |

<210> SEQ ID NO 3
<211> LENGTH: 1001
<212> TYPE: DNA
<213> ORGANISM: Artificial Sequence
<220> FEATURE:
<223> OTHER INFORMATION: synthetic polynucleotide

<400> SEQUENCE: 3

| | |
|---|---|
| caaagtcaag accaggctgg agaaacacac agaaacagca gacctgaaaa aaatgttgca | 60 |

| | |
|---|---|
| catggacccc agactgatag ctgggagtcc agcataggac ttttctagaa accctgaatg | 120 |
| aggatatcag tttggaggtc tggttaatct atggggacac tggtagtgga tcaatattta | 180 |
| tccctagttc atgactggaa tttgggtacc cattccacat ggaggaattc tctgtcagcc | 240 |
| tagacacatg ggggaggttc taggtcctgc tccaaataat gtgttagact ttgaagaact | 300 |
| cccttgagaa gactcaccct ccctggggag cagaaagggg atgggatgag ggttggtgag | 360 |
| ggacaggaga ggaggggagg gtgagggaac tgggattgac aagtaaatga tgcttgtttc | 420 |
| taatttaaat gaataaagga aaagtaaaag aagaaaagaa aacaggccaa aagattataa | 480 |
| aagacagagg tggtgggtga ctataaagaa acactattat ctaaataaaa atatgtcaga | 540 |
| agcacacatg aacttatagt gtttatgaaa gtatgtataa taactacata atctcaagcc | 600 |
| aagaaaaaaa tatcatcttt cagtgatgaa ggtgatttta tttctcccag aattaaagcc | 660 |
| aaagacctaa tgaaagtaat tatcttcaaa aggttgaaaa tacatacttt gcaatacaca | 720 |
| gatctgccta gaaatctcat gttcacaata cacatgatgc tcaattgaat tccattcaat | 780 |
| gttacagttt agataaacag tttgtagata aactcacaat gtatcatttc ttttttatttt | 840 |
| ttgaccaaac agcttctcat ctgttattca gaataattcc tcgatggcag gatatccatc | 900 |
| ccaattgggg gaagggagaa atttgaagaa aacctagacc acatacatat ttgccattgg | 960 |
| gaaacaaagt ctaaaatgat gttgttcaca tcttctctac t | 1001 |

<210> SEQ ID NO 4
<211> LENGTH: 14931
<212> TYPE: DNA
<213> ORGANISM: Cricetulus griseus
<220> FEATURE:
<221> NAME/KEY: misc_feature
<222> LOCATION: (2176)..(2239)
<223> OTHER INFORMATION: n is a, c, g, t or nucleotide is missing

<400> SEQUENCE: 4

| | |
|---|---|
| catgtacact tatgcaagta tgatatggcc caacacagta ttttacacca attttttatct | 60 |
| ataaaatata catgtacatc aaaatatatt attaataata acatcattat tctttctttc | 120 |
| caagtaataa acacatacac tgaaattttg gttcttgtgg ataattttaa tgaaacagga | 180 |
| aatgcaaatt tatcttagca tgtttacttc actttctttg catagataac cagtaatcac | 240 |
| attgatggat catgtagtga aatgtatttt taggtatcta aggaattttg gcttcgtttt | 300 |
| gtgcttgttg acactgaatt ctattcctaa caacagtgtg taaggattct gtctgatttc | 360 |
| ttttaccagt atttgtccat ttgcattttc tttattattc atggctgctg ttctagaaag | 420 |
| tggaaggtag tgtgtcaagt ctgtttaaca tgtttccctg atgatcagtg tcttaacacc | 480 |
| tctctgagta catgttggcc aatgtcgttt ctagacccat ctattcttgc ttgacttatc | 540 |
| ctggtacatg cctgccaaga aatttctcct catcctttct gtctcttcac tgatttactt | 600 |
| gatgtgtgga tttcacattg atcatatgga aatagaagat acaattttct ttattcacag | 660 |
| tttggaagac tttcaatctc atagatcatc attatttttt gctactgttc cctatgctat | 720 |
| ggtgaaattt ccatttgaat aattgcttaa acaattaaca agaaagaatc tattttttact | 780 |
| tgcaataact tccatttcag aacatttact acactgttac tatatccaaa aactagtttt | 840 |
| atatatcatg tgagaaatga ctaattcata atttggccat gacatttttt tcagaaacag | 900 |
| aaaaagtgac caatacatac acaatgctat aaatattaag acttcagcaa attaaatatt | 960 |
| tattcatgat atcacataaa attcatttat tatgttttat ttaaatgtgt ttttaaaaca | 1020 |
| gtggtatcac taaatattaa gttagatgtg tttatgtgct taatgaattt atattttaga | 1080 |

```
atgttataag ttgtatatag tcaaatatgt aataaatttt attttttagg tctttctcat    1140
taaggtattt taattttggg tcccttttcc agagtgactc tagctcatga tgagttgaca    1200
taaaaactaa acagtacaaa atgtacattg cattcagtat tgcacttgat ctttgcactg    1260
aagtttgagt cagttcatac atttagtact tgggaagtac attaagctaa ctttcattgc    1320
tctggcaaaa tgctcgataa gataagagtc tattgtggaa agccatggca gcaggaaagt    1380
aagactgctg atgatgttta atccatagtc aagacgcaga aggagatgaa tgctggtatc    1440
caacattttt tgctgttcat tttctctaga accctagtcc ataaagatgt atgacttgca    1500
ttcaaaatgc gtccccttca gttgttcaac ttttctgtaa atatcctttc aggcatgtct    1560
agaagattgt ttcgcaaata cttctcaatc cattcaagtt gatagtgcag attaatcact    1620
gcagaataaa agcctgtaac ttggctcacg tgccaaggaa tatgcacact cctgacacat    1680
caataagtaa atcaaagtgt agcttttgcc tttaacattg ccagacttat gtaatgttct    1740
gcacgttctt cctccatcac ttttattct aatggtgttt ccttgacatt gaatcacgct    1800
gtggaagctg cttagaatta acattgaaat ctactgatat atttatgatg cagcaattta    1860
gatttactat tttacttaga attttttata attgagagaa tataatattt tcacagttat    1920
ctatctgctg taaatagagg attttaaaaa aaatctctat aactttttt tacaacacac    1980 agtaaaatta agttaaaatt taataaagtc actatgttga tttcaaagtg tgctacgccc    2040
acggtggtca cgcaggtgta gcagaagatg ccactaaggt gggctaaggc cgatgggttg    2100
gggtctgcgc tccctggaga tgagcccag gcggttccct ggcaatcagc tgcgatcatg    2160
atgcccgatg agccannnnn nnnnnnnnnn nnnnnnnnnn nnnnnnnnnn nnnnnnnnnn    2220
nnnnnnnnnn nnnnnnnnnc tgggtgactt tatggaaaga atttgataga tttcatgatg    2280
tagaagaatt ttattaggct tattttacag gagactaaga ccctgggacc taaagatatc    2340
tgggtcctga gaatcaggaa atgggtagag acgtggttga tggtatgaga cagattttag    2400
agaactctta gatcatgggc aatgaccgca atctgatgct tagaatagat catctataaa    2460
caattatgct gttctttttc tttctgttgt atgatctgat gatgtagccc ccttgccaag    2520
ttccctgatc ccccttgcca agttccctga ttgtaacagt atataagcat tgcttgagag    2580
catattcaac tacattgagt gtgtctgtct gtcatttcct cgccgattcc tgatttctcc    2640
ttgagccttt tccttgttc tccctcggtc ggtggtctcc acgagaggcg gtccgtggca    2700
aaagtgtata atgttctaa acatttgaa ctctaaaaca tgcaaaatga aaaattaaaa    2760
taaataaaca tgaaaattaa aatatattag ctgctaaaag ttaaacaata ctatataata    2820
ttttgttatt agaattcaaa atcacattag ttggatttaa tttgaacatt gcattctttc    2880
aataataatt tcaataaaaa aagtttcccc atgatagtag aaaataataa catatgtatc    2940 tatctatttta tttaactaca catatatagc atttgtttca actaaaataa atgaatgagc    3000
aaagcaccta agtaattggt gtctattata tttatgaagc caatagtttc aaataaatta    3060
tcatgcataa ggaggtattg caaatgttaa accttttttg aaacagatat tcccagttac    3120
agaaattata atttctaatc tttcctataa gtagaatgat gataattaat ataggccatt    3180
tgtaaataat gttcagatta aaatattctc tatttcacta gagaagaatg atattaaatg    3240 tattatatttt tatttcccat tttgtttgca ccactattct atatccctca gcagtttaaa    3300
tttgtttcac catatgtgtg tgtgtttgta tcttaaatat ggcactaaaa ttagaataat    3360
ttaatataaa tctttaggag aaaagatatt gaattatttt atgttgatag gaaaatatct    3420
```

```
tttaattgtc caagaatact tttctcttcta ttttaggact gatcagaccc aggactaata    3480
ttttatatgt actaattcta tgtaccaaaa tatgttatta tctcatgaat tctgtctcaa    3540
tattgaggta ataaaaatag tccatcatga actttaaaat taaaataatg attaattaat    3600
ttttattcat attttgtttg tatgaatggt tatacatcac atgtgtgcct ggtgactgtg    3660
aatgtcagga gaaggtatga aagccactgg aattggaata agagataata tttgagatgt    3720
tatgtgggtg ctgagaatta gacgcaagcc atcttcaaga atagccagca tactatacca    3780
ctgagtaatc cattcatccc tcaataatta tctttgtaga cagtaaatat atttctaaac    3840
tataaatgac cagaaaaatt aatgtattat taatgaagac attcatctca tgtgacacac    3900
ttcacctgtc taaatcagta acactctctc cactaattaa gattttctaa gtgcatgaca    3960
cttactattt ctaaagctgt ccaatggggg ccagtcccca gtcagcaccc agtgagataa    4020
tccatgaatg catttatatc ttaggaaaaa ttcttatcta tgtagtattt agaacatttt    4080
catgtgaggg gataaacaag gaagcacaga tgctttctga tagaaacttt ctctttaatt    4140
catctagaaa aaaaaaacct ctcaggaaaa tctctcttgc tctcctccca atgctctatt    4200
cagcatcttc tccctactta attctagatc ttttctcta tgcctccttg ctgctgccct    4260
gctggctctg ctctatgcct ccccatgtca cttttctttg ctatctcacc gttaccttct    4320
ctgcctcact ctctgccttc ttctctgctt ctcacatggc caggctctgg acaattatag    4380
ttatatgtta cattctcata acacatgata tgtcacatag tttctctcag gctaggata    4440
tcacaatgac tggccaatga gcaagtggcc ttgcatgtag ctctaagttg gtgatggttc    4500
ccagacagta agtagccatt tggttgaaat ttgaggttgg gtagtacatg aagactgaat    4560
tttcttcaaa ctctggcctt gaaatagtaa acaacacct atgaaaatga cgacctgtat    4620
ttgtctttag aggcaaccac atattgtctg cagggcctgc tttgaatttg ctctgaagtt    4680
agcttgtttg tgtaaaagga agaatcctat atcagcctga gaaatgtaaa atatcctagc    4740
atttcaagtc atcaaaatta tatggagagt ataaatcatc cttctgacta ttcatagtca    4800
tatttgtgtc caccaagtat aaaacacact accaaagggc tgtggaaaaa atcgccataa    4860
ctgttcttat tagggaggca tagcagtggt acctgaggaa gttacagcaa caaccagtca    4920
tccagtcaat aaccccatgg ctttgccact tggaggtacc caataatgtt tggctttgcc    4980
gagtaggact ccaacaaatt cagagggtca atttttaaat gctggttgtc actgctgaac    5040
agtcccattg ccctctgcat aattccacaa tggaaagctt tttacactga ttgccaatca    5100
ttaaacagcc tactcagcat aaacaggtat gatattattc tgcattttgt tacattacta    5160
gatgaattcc tatttcttcc tacaatagtg gaactgaaaa aagatacaca atcatactac    5220
ccctctacta atcttatgac ttatatcatt tcaattttca gaccataatg caaactattg    5280
accaaaacat gtgaagatga aaaatagaaa tgtagaataa tattacatat aaaaagaaaa    5340
ggcggactta ttttgtttta tttcttagca tgcatagcaa tacatgattt gaggtttata    5400
taataaaggg acaataaatc ttcaagaaac ttaccctac tgaattaaaa tattaaagaa    5460
ggtcacacat ttactcaaat atattagact actgggcaaa tagacatgaa agtagagtt    5520
aatattgagg taggccttct gtgaaatgtc taaggaaatt atgttcata cagtgtgtaa    5580
ccaagtggga atcatatcag aaagcagtca aaagcttata ttacaagtaa cagatgcttg    5640
gttatatgac ctcccagagc ttgactgtct atacacaaaa agtggtgtta ataaaactgt    5700
aatttgggct atgttttttt aaatggcttc accaacatga aaggaaggga atgagcatgt    5760
catggatgct tagagattat gcttccagca agaagaattg agctttggct cttattacag    5820
```

```
aaacatgaca aggtgtgagt tttatttatt agaaattata taatatttta agctggggac    5880
taaaaatttt attgaaacaa acaggcaagg gataggcatg tactagaagc aaaaatagga    5940
tgtcaatgct gtaatgttat tttttggacc aaaatagtat ttcctataga aatgacaatg    6000
atcttaggtt attattcttc ataaagatga caagttcaca agatatccta gttcattaaa    6060
atcgttttag tcatttaata gagtgctgtg atagattaca caaaggaaag cacttacgat    6120
gagaaataat gatatccaca attatttct  taattcttag aaacattcta ttgttatatc    6180
tcaatctcag aagccactta ttgctttatt attgaaacat atgaaattgt aagttatata    6240
ttgtctatgg tgacatttca aagaacatgt gacgtacagt gtagcacaga taaagaacat    6300
aactgcagct gaatcagtaa ctaaacttac atacattaaa tctgccatgt tggcaacagt    6360
gtgtgcacta ccaaaggatg tactaatgct cacgacactc ccctatgtca cccttttgttc   6420 atcattacat cataggtcta ttttgtttgc ttttgaaatc tagaccaagt cttttgtgtc    6480
tttccaagca cagagctcat taatttacct catagacttg ttaaacttct tctggttcat    6540
caattgaata gaaatactca ctactaatta tgtgagaccc tgccagtacc atagcacatg    6600 gataatttt  acataaaaca tgcatacaag taagattatt cagactgaac atgaattta    6660 gagaaatcag gaaggagtat atgggagtgg ttggagtgag actagagaaa tgtaattaaa    6720
ctataatctc aatacaaaga tctactaagc aaaaaacatg aaacattgtc attcaagtga    6780
aacatcagtc ttcaaattgg aaagatattt ttactaggaa aatgtctggt agatggttat    6840
tatctagaaa acacaaaaat tagaaaacgg taaactttaa taaaagaat  aatacaatga    6900 gactacatga aaagttctta actaatgaaa caaatatctt gaactttttt tcttaaaagt    6960
ttaatatcaa taaccatcat ggaaattcaa attaaaacta tttacatatt accctgaaa   7020 taataactaa tacccaataa aaataatata aacaaaaaat ggcaatgcat gccatcatgg     7080
atttgggaga gagaatgttc attgcagttc tgaatggata ctggtgccac cacggtgaaa    7140
atctctgtat aggtccttcc aaaagctgaa aatagacata tcacaagacc tgccacacat    7200
ttttcaagca aatacccaaa ggactctacc tgactgcaga gacactttct cataaaatat    7260
tattgttgat ctattcataa tatctggaaa atagaaacag ccaagatgcc catcaactga    7320
ttaatagatg ataaaattat tgtacatttc agtgtaatat tattcagttt ttaagaaaaa    7380
tgaaattatg taataagcat gtaaatggat atatcttgaa acaaccattc cccattatat    7440
tacctaaaca ttgaaagtcc aaaatcatat gatctttta  gtggatctac taatcttttg    7500
ctatatgtat tttattgaac tacccatgga tgtgagataa ttggtaacaa cagcacatgg    7560
gagagcatgg gatcattcaa ggaagattag agagaatgca ttttttagga gataatggag    7620
gagcaataga aaggattaaa tgaggttact gatgaaagtg atggttagag aaggcaatat    7680
gaggagggat aactagcact tagggccttt tgaaaaagac atagagaaaa tactattgta    7740
gaaacttcct ataattggtg tatagttata tacaccaaag agctcagatg gagttacccct   7800 ataatggaaa tattaactac tttttatcac tgtgataaaa catcctgaac agagcaacat    7860
agattgggaa gcatttactt tggcttacag ttctaacggg ataaaaattc atgatgaaag    7920
aatgaatatg tcagcaaaca gcagtagcaa tggcctgaga agcaggtgag agctcacatc    7980
ttgaagtgta agaatgtagc agagagaaca aactgcaaat gaccagaaaa tgcttttgga    8040
tcagagccca taccctctg  actgacttct ccagaaattc tgaacaaata aaactccccca  8100 aacagagcca taactgaagg tccagtgtct gagactacta ggggtatttc ttattcaaac    8160
```

```
cactacaatg gggtgggggg agcaatcctc caagtaggca ctacacacag acaaataaaa    8220
actctagtaa ctggaatgga ttgacttatt tgaattactt gccagtggag ctacatagag    8280
cacaattatt gtatttaaat taccctttat gatcttacaa aacttgacag taagatcata    8340
ttgctaaaga aaccacatat ttgaatcagg gaacatggtg atatctagtt gttcttcaac    8400
tggaaacttc atgctttctg cccagcattc atgttgctgg aaagagcaat gtacactacc    8460
agtgtagaaa ttaaatcatc aatcttatca agatgtggat cctataagtt acaataaaaa    8520
ttagcctgat aagatatccc caccagaaga atattcacat aaatgctatg ggagcaacaa    8580
gctattttct aaattagctt taatcctatt ctacaagaga gaatccatat ctagaatagt    8640
tatagggatc aagaacccat ggcttgattg gtcataggcc caatgggaga tcctaatatt    8700
attgttctac aaaatgaaaa taactcctaa tgacttgttg ctgcagtaat aagttagtat    8760
gttgctcaac tctcacaaga gaagttttgt cttacaataa atggcaatta aagcagcccc    8820
acaagattta tatcataccg atctcctcat ggcctatgca tctagaagct aggaaacaaa    8880 gaggaccta agagagacat acatggtccc cctggagaag gggaaggggg caagacctcc    8940
aaagctaatt gggagcatgg gggaggggag agggagttag aagaaagaga aggggataaa    9000
aggagggaga ggaggacaag agagagaagg aagatctagt caagagaaga tagaggagag    9060
caagaaaaga gataccatag tagagggagc cttgtatgtt taaatagaaa actggcacta    9120
gggaattgtc caaagatcca caaggtccaa ctaataatct aagcaatagt cgagaggcta    9180
ccttaaaagc ctttctctga taatgagatt gatgactacc ttatatacca tcctagagcc    9240
ttcatccagt agctgatgga agcagaagca gacatctaca gctaaacact gagctagttg    9300
cagacaggga ggagtgatga gcaaagtcaa gaccaggctg gagaaacaca cagaaacagc    9360
agacctgaaa aaaatgttgc acatggaccc cagactgata gctgggagtc cagcatagga    9420
cttttctaga aaccctgaat gaggatatca gtttggaggt ctggttaatc tatggggaca    9480
ctggtagtgg atcaatattt atccctagtt catgactgga attttgggtac ccattccaca    9540 tggaggaatt ctctgtcagc ctagacacat ggggagggtt ctaggtcctg ctccaaataa    9600
tgtgttagac tttgaagaac tcccttgaga agactcaccc tccctgggga gcagaaaggg    9660
gatgggatga gggttggtga gggacaggag aggaggggag ggtgagggaa ctgggattga    9720
caagtaaatg atgcttgttt ctaatttaaa tgaataaagg aaaagtaaaa gaagaaaaga    9780
aaacaggcca aaagattata aaagacagag gtggtgggtg actataaaga aacactatta    9840
tctaaataaa aatatgtcag aagcacacat gaacttatag tgtttatgaa agtatgtata    9900
ataactacat aatctcaagc caagaaaaaa atatcatctt tcagtgatga aggtgatttt    9960
atttctccca gaattaaagc caaagaccta atgaaagtaa ttatcttcaa aaggttgaaa   10020
atacatactt tgcaatacac agatctgcct agaaatctca tgttcacaat acacatgatg   10080
ctcaattgaa ttccattcaa tgttacagtt tagataaaca gtttgtagat aaactcacaa   10140
tgtatcattt cttttatttt tttgaccaaa cagcttctca tctgttattc agaataattc   10200
ctcgatggca ggatatccat cccaattggg ggaaggggag aatttgaaga aaacctagac   10260
cacatacata tttgccattg ggaaacaaag tctaaaatga tgttgttcac atcttctcta   10320
ctagtcctct ccccgtccca aagaaccttg gtatatgtgc ctcatttac agagagagga   10380 aagcaggaac tgagcatccc ttacttgcca tcctcaaccc aaaatttgca tcattgctca   10440
gctctgccct tctcatatga cagttacaag tcaaggcttc caaagtccct ctgtcatgtt   10500
tggtgtcaat agtttataca gatgacttca tgtcttcata tctaatgtct tatatagatt   10560
```

```
aatattaaac aatgttattt ctctaaccac attttaaatt aatttaaaaa tccattaatt    10620
gtgtctataa aatgcagaca gagtgctgag acacaatata agcctgatga tctgaatttg    10680
aaactcacac ccaccacatg gagaatcaac ttccaaaaat tttcctatta cttccacact    10740
tacaccattg tacaaacaca ataataatga acaaaatgaa atgaaataaa aaattaagtc    10800
tctgtaggta atgctactgt gcagcaaaag taaaaatggc agcttaagct tgctttatgg    10860
ttacacttta ccatcttcca ttaattataa ggacttcaat catggcagaa ctatgctgtt    10920
attgtctcag tgtaacctaa ccaggtgttc cagatgttct taatgtggac acctaaacta    10980
tttgatattt gggttaagat cttttccctct ttcagaagaa acctcaggac agagggaatc    11040
ttgtctttta attttgagtc tgtagacttt ttccatttca aatatacatg aaacaagtga    11100
tgaagaaaat taatcaaaag gtgggaattg caatgatatt aggttcaata ttaagcttca    11160
atattatcat ggaatcgcct gttatacact gagtgtttgg caataaggga tttttagaag    11220
aaggagtttt tattctcaac aggttcctta agtttagctc aaataaatct aagcaatcca    11280
ctctagaatt aaatagtttc ctaagggcac agctatgaat agagctcaat ttacatataa    11340
aattttgttc accatttatg tcattccagt tttcattagt acaaggaaaa tacaaaatat    11400
ttagatgtca atatcaagtg aatagttcat ctccttttt aatatatatc acctaaatca    11460
ccattttctc agaaaaatct ggcctgaagt tctgtctgga acttcaacat gaaaaatatg    11520
cacagcttgc tattataaat cctagttgat ttttaagatt catgtctggt gtctgactca    11580 gagggggccag aggctagaca aatattttt gaatcttcat tgtgaagatt tttaatgatt    11640 atttaatat aaataacaaa gatgatggat aatgtaactt tgtacagttc atagacgctg    11700
aactactttg tgcttaaaat gttagttccc tatcataaat gataggtgat aagtgtatgt    11760
ttaatacttt ccctctgagc tatattcatg tactagagaa ttattttaaa catgaaaaga    11820
ctgtgtttat agtctcagct cctgagaact ggtccaacct taggcaggtg aatgccagga    11880
gcaacgtttt tcttctacag aggatgcttt gctgccaagc aacctggttg tgtggaaatg    11940
ttcctttttt aatcaagttt aaagggtctt catcatgctg ttgctccaca tattttcagg    12000
ttagagcttg gtccttggag tattatcttt taccagaaaa ttcatagtat tcttcaata    12060 actaacaact aaacttttcg ataaaaaaga attggaattt caattttaaa gcctgagtaa    12120
aattcttgtg aatcaggata ttttatttta agtcttatct tttaaaaagt tattttattt    12180
tttaaaaaat tataatatac tttcataatt tccctccttc acttttcttt acaaacactt    12240
ctatagatca ccatgtgttt ttttttttac atttatggcc tctttctgtt cattgttatt    12300
acatacaaat agtcttgcct atagaagaac accacaattt gttacctgat aacaaattat    12360
caacccttaa aacctacaaa ctattgatat tactgaaaag actatactta tagatgtaaa    12420
gatatatgtg tgtgcacata tatagataca catatatgta ggattttaa ttttagattt     12480 tagacatcaa aattatttat atgactgaga aactagacac tataaatgag cattcagtat    12540
tcaacaccgt gattttagat attgtcacaa tgacagaaaa ttttcttata gaaaattta    12600 agttttgtga ttgctctgtg cacttagtga agtctcacag aaaaagaatc atagtatttt    12660
tagtttataa taaaaagtac atataattaa aatggttggc acaaacaac atttgagcat    12720 ttttcctatt tactatcaag tagtatcatt ttgaaataat aatttgacta gtttcaaaaa    12780
tgaaaacaaa atttaaacta aatgcctaat ctagcctgat aacattttta tgaatgaaat    12840
tattcaatag tgttatcaat tagggcccca aaacttttcc taaaataaaa ctttaatt    12900
```

```
ttttccattt ttatttaaat tagaaacaaa attgttttac atgtaaatca gagtttcctc    12960
accctcccct tctccctgtc cctcactaac accctacttg tcccatacca tttctgctcc    13020
ccagggaggg tgaggccttc catggggaaa cttcagagtc tgtctatcct ttcggatagg    13080
gcctaggccc tcacccattt gtctaggcta aggctcacaa agtttactcc tatgctagtg    13140
ataagtactg atctactaca agagacacca tagatttcct aggcttcctc actgacaccc    13200
atgttcatgg ggtctggaac aatcatatgc tagtttccta ggtatcagtc tggggaccat    13260
gagctccccc ttgttcaggt caactgtttc tgtgggtttc accaccctgg tcttgactgc    13320
tttgctcatc actcctccct ttctgtaact gggttccagt acaattccgt gtttagctgt    13380
gggtgtctac ttctactttc atcagcttct gggatggagc ctctaggata gcatacaatt    13440
agtcatcatc tcattatcag ggaagggcat ttaaagtagc ctctccattg ttgcttggat    13500
tgttagttgg tgtcatcttt gtagatctct ggacatttcc ctagtgccag atatctcttt    13560
aaacctacaa gactacctct attatggtat ctcttttctt gctctcgtct attcttccag    13620
acaaaatctt cctgctccct tatattttcc tctcccctcc tcttctcccc ttctcattct    13680
cctagatcca tcttcccttc ccccatgctc ccaagagaga tgttgctcag gagatcttgt    13740
tccttaaccc ttttcttggg gatctgtctc tcttagggtt gtccttgttt cctagcttct    13800
ctggaagtgt ggattgtaag ctggtaatca tttgctccat gtctaaaatc catatatgag    13860
tgatgtttgt cttttttgtga ctgggttacc tcactcaaaa tggtttcttc catatgtctg    13920
tggatttcaa tagcacaaac aacatacagt atcttggggc aacactaacc aaacaagtga    13980
aagaccagta tagcaagaac tttgagttta aagaaagaaa ttaaagaaga taccagaaaa    14040
tggaaagatc tcccatgctc tttgataggc agaatcaaca tagtaaaaat ggcaatcttg    14100
ccaaaatcca tctacagact caatgcaatc cccattaaat accagcacac ttcttcacag    14160
acctgaaaga ataatactta actttatatg gagaaacaaa agcccagga taggccaaac    14220 aaccctgtac aatgaaggca cttccagagg catccccatc cctgacttca agctctatta    14280
tagagtaata atcctgaaaa cagcttggta atggcacaaa aatagacagg tagaccaatg    14340
gaattgagtt gaaaaccctg atattaaccc acatatctat gaacacctga ctttgacaaa    14400
gaagctaagg ttatacaatg taagaaagaa agcatcttca acaaatcgtg ctggcataac    14460
tggatgctgg catgtagaag actgcagata gatccatgtc taatgccatg cacaaaactt    14520
aagtccaaat ggatcaaaaa cctcaacata aatccagcca cactgaacct catagaagag    14580
aaagtgggaa gtatccttga ataaattggt acaggagacc acatcttgaa cttaacacca    14640
gtagcacaga caatcagatc aataatcaat aaatgggacc tcctgaaact gagaagcttc    14700
tgtaaggcaa tggataagtc aacaggacaa aatggcagcc cacggaatgg gaaaagatat    14760
tcaccaatcc tatatctgac agagggctgc tctctatttg caaagaacac aataagctag    14820
tttttaaaac accaattaat ccgattataa agttgggtag agaactaaat aaagaattgt    14880
taacagagca atctaacttg gcagaaagac acataagaaa gtgctcacca t             14931
```

<210> SEQ ID NO 5
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 5
tgagctagtt gcagacaggg                                                 20

```
<210> SEQ ID NO 6
<211> LENGTH: 79
<212> TYPE: RNA
<213> ORGANISM: Artificial Sequence
<220> FEATURE:
<223> OTHER INFORMATION: synthetic polynucleotide

<400> SEQUENCE: 6
guuuuagagc uagaauagca aguuaaaaua aggcuagucc guuaucaacu ugaaaaagug          60
gcaccgaguc ggugcuuuu                                                      79
```

CHO INTEGRATION SITES AND USES THEREOF

CROSS REFERENCE TO RELATED APPLICATIONS

This application is a continuation of U.S. patent application Ser. No. 16/575,506, filed Sep. 19, 2019, which is a continuation of U.S. patent application Ser. No. 15/783,525, filed Oct. 13, 2017, now abandoned, which is a continuation of U.S. patent application Ser. No. 14/919,300, filed Oct. 21, 2015, now U.S. Pat. No. 9,816,110, which claims the benefit of priority of U.S. Provisional Application No. 62/067,774 filed Oct. 23, 2014, the entire contents of which are incorporated herein by reference.

INCORPORATION BY REFERENCE OF SEQUENCE LISTING

The Sequence Listing in an ASCII text file, named 32353_T0045US01_SequenceListing.txt of 28 KB, created on Oct. 20, 2015, and submitted to the United States Patent and Trademark Office via EFS-Web, is incorporated herein by reference.

BACKGROUND

Field of the Invention

The invention provides for stable integration and/or expression of recombinant proteins in eukaryotic cells. In particular, the invention includes methods and compositions for improved expression of proteins in eukaryotic cells, particularly Chinese hamster (*Cricetulus griseus*) cell lines, by employing expression-enhancing nucleotide sequences. The invention includes polynucleotides and modified cells that facilitate recombination-mediated cassette exchange (RMCE). The methods of the invention integrate exogenous nucleic acids at specific chromosomal loci in the Chinese hamster cellular genome in order to facilitate enhanced and stable expression of recombinant proteins by the modified cells.

Description of Related Art

Cellular expression systems aim to provide a reliable and efficient source for the manufacture of a given protein, whether for research or therapeutic use. Recombinant protein expression in mammalian cells is a preferred method for manufacturing therapeutic proteins due to, for example, the ability of mammalian expression systems to appropriately post-translationally modify recombinant proteins.

Several cellular systems are available for expression of proteins, each containing various combinations of cis- and, in some cases, trans-regulatory elements to achieve high levels of recombinant protein with short incubation times. Despite the availability of numerous systems, the challenge of efficient gene transfer and stability of the integrated gene for expression of a recombinant protein still exists. Multiple local genetic factors will determine not only when the target gene of interest is to be expressed, but whether the cell can functionally drive the transcription of the gene towards a productive output, or whether the expression will even be sustained long-term. Chromosomal integration sites, e.g. Chinese hamster ovary cell (CHO) integration sites and locus control regions within or adjacent to specific genes have been characterized in the art (WO2012/138887A1; U, Q. et al., 2002 *Blood.* 100:3077-3086). As such, targeted regulatory regions are typically identified in a region coding for endogenous proteins. However, for long-term expression of a target transgene, a key consideration is minimal disruption of cellular genes to avoid changes in the phenotype of the cell line.

Engineering stable cell lines to accommodate additional genes for expression, such as additional antibody chains as in multispecific antibodies, is particularly challenging. Wide variations in expression levels of integrated genes may occur. Integrating additional genes may lead to greater variation in expression and instability due to the local genetic environment (i.e., position effects). Accordingly, there is a need in the art for improved mammalian expression systems.

BRIEF SUMMARY

In one aspect, the invention provides a cell comprising an exogenous nucleic acid sequence integrated at a specific site within a locus, wherein the locus comprises a nucleotide sequence that is at least 90% identical to SEQ ID NO:1 or SEQ ID NO: 4. In some embodiments, the locus comprises a nucleotide sequence that is at least 90% identical to SEQ ID NO:1. In some embodiments, the locus comprises a nucleotide sequence that is at least 90% identical to SEQ ID NO:4.

In another aspect, the invention provides a polynucleotide comprising a first nucleic acid sequence integrated into a specific site within a second nucleic acid sequence (e.g. a locus of the invention). In one embodiment, the second nucleic acid sequence comprises the nucleotide sequence of SEQ ID NO:1. In another embodiment, the second nucleic acid sequence comprises the nucleotide sequence of SEQ ID NO:4.

In one embodiment, the second nucleic acid sequence is an expression-enhancing sequence selected from a nucleotide sequence having at least 90% nucleic acid identity to SEQ ID NO:1, or an expression-enhancing fragment thereof. In one embodiment, the second nucleic acid sequence is an expression-enhancing sequence selected from a nucleotide sequence having at least 90% nucleic acid identity to SEQ ID NO:4, or an expression-enhancing fragment thereof. In another embodiment, the expression-enhancing sequence is capable of enhancing expression of a protein encoded by an exogenous nucleic acid sequence. In another embodiment, the expression-enhancing sequence is capable of enhancing expression of a protein encoded by an exogenous nucleic acid sequence at least about 1.5-fold to at least about 3-fold enhancement in expression compared to expression typically observed by random integration into a genome.

In another embodiment, the exogenous nucleic acid sequence is integrated into a specific site at any position within SEQ ID NO:1 or SEQ ID NO:4.

In some embodiments, the specific site at a position within SEQ ID NO:1 or adjacent to a position within SEQ ID NO:1 is selected from the group consisting of nucleotides spanning positions numbered 10-4,000; 100-3,900; 200-3,800; 300-3,700; 400-3,600; 500-3,500; 600-3,400; 700-3,300; 800-3,200; 900-3,100; 1,000-3,000; 1,100-2,900; 1,200-2,800; 1,300-2,700; 1,200-2,600; 1,300-2,500; 1,400-2,400; 1,500-2,300; 1,600-2,200; 1,700-2100; 1,800-2050; 1850-2050, 1,900-2040; 1950-2,025, 1990-2021, 2002-2021 and 2,010-2,015 of SEQ ID NO:1. In certain embodiments, the specific site at a position within SEQ ID NO:1 or adjacent to a position within SEQ ID NO:1 is selected from the group consisting of nucleotides spanning positions numbered 1990-1991, 1991-1992, 1992-1993, 1993-1994, 1995-1996, 1996-1997, 1997-1998, 1999-2000, 2001-2002, 2002-2003, 2003-2004, 2004-2005, 2005-2006, 2006-2007, 2007-2008, 2008-2009, 2009-2010, 2010-2011, 2011-2012, 2012-2013, 2013-2014, 2014-2015, 2015-2016, 2016-2017, 2017-2018, 2018-2019, 2019-2020, and 2020-2021 of SEQ ID NO:1.

In another embodiment, the specific site at a position within SEQ ID NO:1 or adjacent to a position within SEQ ID NO: is selected from the group consisting of nucleotides spanning positions numbered 10-500; 500-1,000; 500-2,100; 1,000-1,500; 1,000-2,100; 1,500-2,000; 1,500-2,500; 2,000-2,500; 2,500-3,000; 2,500-3,500; 3,000-3,500; 3,000-4,000; and 3,500-4,000 of SEQ ID NO:1. In certain embodiments, the exogenous nucleic acid sequence is integrated at, within or near any one or more of the specific sites described above.

In another embodiment, the exogenous nucleic acid sequence comprises a recognition site positioned within an expression-enhancing sequence as described above, providing that the expression-enhancing sequence comprises a sequence that is at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the expression-enhancing sequence of SEQ ID NO:1 or SEQ ID NO:4, an expression-enhancing fragment thereof.

In one embodiment, the exogenous nucleic acid sequence comprises a recombinase recognition site. In some embodiments, the exogenous nucleic acid sequence further comprises at least one recombinase recognition site comprising a sequence independently selected from a LoxP site, a Lox511 site, a Lox2272 site, Lox2372, Lox5171, Loxm2, Lox71, Lox66, LoxFas and a frt site. In one embodiment, the recombinase recognition site is integrated within the expression-enhancing sequence. In another embodiment, the recombinase recognition site is immediately adjacent in the 5' direction to the terminal nucleotide of the 5' end of a gene cassette, or immediately adjacent in the 3' direction to the terminal nucleotide of the 3' end of a gene cassette. In some embodiments, the at least one recombinase recognition site and gene cassette are integrated within the expression-enhancing sequence.

In one embodiment, at least two recombinase recognition sites are present within the expression-enhancing sequence. In another embodiment, two recombinase recognition sites of opposite orientation are integrated within the expression-enhancing sequence. In another embodiment, three recombinase recognition sites are integrated within the expression-enhancing sequence.

In one aspect, an isolated Chinese hamster ovary (CHO) cell is provided that comprises an engineered expression-enhancing sequence of SEQ ID NO:1 or an expression-enhancing fragment thereof. In one embodiment, the expression-enhancing sequence comprising the nucleotide sequence of SEQ ID NO:1 or SEQ ID NO:4, or a stable variant thereof, is engineered to integrate an exogenous nucleic acid sequence as described above. In other embodiments, the invention provides an isolated CHO cell comprising an exogenous nucleic acid sequence inserted into a locus comprising an expression-enhancing sequence of SEQ ID NO:1, or SEQ ID NO:4, or a stable variant thereof.

In one embodiment, the CHO cell further comprises at least one recombinase recognition sequence within the expression-enhancing sequence. In another embodiment, the at least one recombinase recognition sequence is independently selected from a LoxP site, a Lox511 site, a Lox2272 site, Lox2372, Lox5171, Loxm2, Lox71, Lox66 LoxFas and a frt site. In another embodiment, the recombinase recognition site is immediately adjacent in the 5' direction to the terminal nucleotide of the 5' end of a gene cassette, or immediately adjacent in the 3' direction to the terminal nucleotide of the 3' end of a gene cassette. In some embodiments, the at least one recombinase recognition site and gene cassette are integrated within the expression-enhancing sequence of the CHO cell genome described herein.

In another embodiment, the at least one recombination recognition site is positioned as described above, with the caveat that the gene cassette comprises an expression-enhancing sequence comprising at least 90% identity, at least about 91% identity, at least about 92% identity, at least about 93% identity, at least about 94% identity, at least about 95% identity, at least about 96% identity, at least about 97% identity, at least about 98% identity, or at least about 99% identity to nucleotides 1001 through 2001 of SEQ ID NO:1 (SEQ ID NO:2) or an expression-enhancing fragment thereof. In another embodiment, the at least one recombination recognition site is positioned as described above, with the caveat that the gene cassette comprises an expression-enhancing sequence comprising at least 90% identity, at least about 91% identity, at least about 92% identity, at least about 93% identity, at least about 94% identity, at least about 95% identity, at least about 96% identity, at least about 97% identity, at least about 98% identity, or at least about 99% identity to nucleotides 2022 through 3022 of SEQ ID NO:1 (SEQ ID NO:3) or an expression-enhancing fragment thereof.

In yet another embodiment, the at least one recombinase recognition site is inserted in the CHO cell genome at or within nucleotides 1990-1991, 1991-1992, 1992-1993, 1993-1994, 1995-1996, 1996-1997, 1997-1998, 1999-2000, 2001-2002, 2002-2003, 2003-2004, 2004-2005, 2005-2006, 2006-2007, 2007-2008, 2008-2009, 2009-2010, 2010-2011, 2011-2012, 2012-2013, 2013-2014, 2014-2015, 2015-2016, 2016-2017, 2017-2018, 2018-2019, 2019-2020, 2020-2021 or 2021-2022 of SEQ ID NO:1.

In another embodiment, the exogenous nucleic acid is inserted in the CHO genome at or within nucleotides 1990-1991, 1991-1992, 1992-1993, 1993-1994, 1995-1996, 1996-1997, 1997-1998, 1999-2000, 2001-2002, 2002-2003, 2003-2004, 2004-2005, 2005-2006, 2006-2007, 2007-2008, 2008-2009, 2009-2010, 2010-2011, 2011-2012, 2012-2013, 2013-2014, 2014-2015, 2015-2016, 2016-2017, 2017-2018, 2018-2019, 2019-2020, 2020-2021 or 2021-2022 of SEQ ID NO:1.

In another embodiment, the exogenous nucleic acid is inserted in the CHO genome at or within nucleotides 2001-2022 of SEQ ID NO:1. In some embodiments, the exogenous nucleic acid is inserted at or within nucleotides 2001-2002 or nucleotides 2021-2022 of SEQ ID NO:1 and nucleotides 2002-2021 of SEQ ID NO:1 are deleted, as a result of the insertion. Likewise, the exogenous nucleic acid is inserted in the CHO genome at or within nucleotides 9302-9321 of SEQ ID NO:4. In some embodiments, the exogenous nucleic acid is inserted at or within nucleotides 9301-9302 or nucleotides 9321-9322 of SEQ ID NO:4 and nucleotides 9302-9321 of SEQ ID NO:4 are deleted, as a result of the insertion.

In some embodiments, the exogenous nucleic acid sequence integrated at a specific site within a locus, such as the nucleotide sequence of SEQ ID NO:1 or SEQ ID NO:4, comprises a gene of interest (GOI) (e.g., a nucleotide sequence encoding a protein of interest or "P"). In certain embodiments, the exogenous nucleic acid sequence comprises one or more genes of interest. In some embodiments, the one or more genes of interest are selected from the group consisting of a first GOI, a second GOI and a third GOI.

In some embodiments, the exogenous nucleic acid sequence integrated at a specific site within a locus, such as the nucleotide sequence of SEQ ID NO:1 or SEQ ID NO:4, comprises a GOI and at least one recombinase recognition site. In one embodiment, a first GOI is inserted within the expression-enhancing sequence of SEQ ID NO:1 or SEQ ID NO:4, or the expression-enhancing sequence having at least 90% nucleotide identity to SEQ ID NO:1 or SEQ ID NO:4, or the expression-enhancing fragment thereof, as described above, and the first GOI is optionally operably linked to a promoter, wherein the promoter-linked GOI (or the GOI) is flanked 5' by a first recombinase recognition site and 3' by a second recombinase recognition site. In another embodiment, a second GOI is inserted 3' of the second recombinase recognition site, and the second GOI is flanked 3' by a third recombinase recognition site.

In yet another embodiment, the GOI is operably linked to a promoter capable of driving expression of the GOI, wherein the promoter comprises a eukaryotic promoter that can be regulated by an activator or inhibitor. In other embodiments, the eukaryotic promoter is operably linked to a prokaryotic operator, and the eukaryotic cell optionally further comprises a prokaryotic repressor protein.

In another embodiment, one or more selectable markers are included between the first and the second and/or the second and the third recombinase recognition sites. In some embodiments, the first and/or the second genes of interest and/or the one or more selectable markers are operably linked to a promoter, wherein the promoter may be the same or different. In another embodiment, the promoter comprises a eukaryotic promoter (such as, for example, a CMV promoter or an SV40 late promoter), optionally controlled by a prokaryotic operator (such as, for example, a tet operator). In other embodiments, the cell further comprises a gene encoding a prokaryotic repressor (such as, for example, a tet repressor).

In another embodiment, the cell further comprises a gene capable of expressing a recombinase. In some embodiments, the recombinase is a Cre recombinase.

In one aspect, a CHO host cell is provided, comprising an expression-enhancing sequence selected from SEQ ID NO:1 or SEQ ID NO:4, or an expression-enhancing sequence having at least 90% nucleotide identity to SEQ ID NO:1 or SEQ ID NO:4, or an expression-enhancing fragment thereof, comprising a first recombinase recognition site followed by a first eukaryotic promoter, a first selectable marker gene, a second eukaryotic promoter, a second selectable marker gene, and a second recombinase recognition site. In more embodiments, the CHO host cell further provides a third eukaryotic promoter, a third marker gene, and a third recombinase recognition site. In one embodiment, the expression-enhancing sequence is within SEQ ID NO:1 or SEQ ID NO:4 as described above.

In one embodiment, the first, second, and third recombinase recognition sites are different from each other. In some embodiments, the recombinase recognition sites are selected from a LoxP site, a Lox511 site, a Lox2272 site, Lox2372, Lox5171, Loxm2, Lox71, Lox66, LoxFas and a frt site.

In one embodiment, the first selectable marker gene is a drug resistance gene. In another embodiment, the drug resistance gene is a neomycin resistance gene or a hygromycin resistance gene. In another embodiment, the second and third selectable marker genes encode two different fluorescent proteins. In one embodiment, the two different fluorescent proteins are selected from the group consisting of Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein (e.g. mKate, mKate2, mPlum, mRaspberry or E2-crimson).

In one embodiment, the first, second, and third promoters are the same. In another embodiment, the first, second, and third promoters are different from each other. In another embodiment, the first promoter is different from the second and third promoters, and the second and third promoters are the same. In more embodiments, the first promoter is an SV40 late promoter, and the second and third promoters are each a human CMV promoter. In other embodiments, the first and second promoters are operably linked to a prokaryotic operator.

In one embodiment, the host cell line has an exogenously added gene encoding a recombinase integrated into its genome, operably linked to a promoter. In another embodiment, the recombinase is Cre recombinase. In another embodiment, the host cell has a gene encoding a regulatory protein integrated into its genome, operably linked to a promoter. In more embodiments, the regulatory protein is a tet repressor protein.

In one embodiment, the first GOI and the second GOI encode a light chain, or fragment thereof, of an antibody or a heavy chain, or fragment thereof, of an antibody. In another embodiment, the first GOI encodes a light chain of an antibody and the second GOI encodes a heavy chain of an antibody.

In certain embodiments, the first, second and third GOI encode a polypeptide selected from the group consisting of a first light chain, or fragment thereof, a second light chain, or fragment thereof and a heavy chain, or fragment thereof. In yet another embodiment, the first, second and third GOI encode a polypeptide selected from the group consisting of a light chain, or fragment thereof, a first heavy chain, or fragment thereof and a second heavy chain, or fragment thereof.

In one aspect, a method is provided for making a protein of interest, comprising (a) introducing into a CHO host cell a gene of interest (GOI), wherein the GOI integrates into a specific locus comprising a nucleotide sequence that is at least 90% identical to SEQ ID NO:1 or SEQ ID NO:4; (b) culturing the cell of (a) under conditions that allow expression of the GOI; and (c) recovering the protein of interest. In one embodiment, the protein of interest is selected from the group consisting of a subunit of an immunoglobulin, or fragment thereof, and a receptor, or ligand-binding fragment thereof. In certain embodiments, the protein of interest is selected from the group consisting of an antibody light chain, or antigen-binding fragment thereof, and an antibody heavy chain, or antigen-binding fragment thereof.

In some embodiments, the GOI is introduced into the cell employing a targeting vector for recombinase-mediated cassette exchange (RMCE) and the CHO host cell genome comprises at least one exogenous recognition sequence within the specific locus. In other embodiments, the CHO host cell genome comprises at least one exogenous recognition sequence and a selectable marker, optionally linked to a promoter, IRES and/or polyadenylation (polyA) sequence, within the specific locus.

In certain embodiments, the CHO host cell genome comprises one or more recombinase recognition sites as described above, and the GOI is introduced into the specific locus through the action of a recombinase that recognizes the recombinase recognition site.

In another embodiment, the GOI is introduced into the cell employing a targeting vector for homologous recombination, and wherein the targeting vector comprises a 5' homology arm homologous to a sequence present in the specific locus, a GOI, and a 3' homology arm homologous to a sequence present in the specific locus. In another embodiment, the targeting vector further comprises two, three, four, or five or more genes of interest. In another embodiment, one or more of the genes of interest are operably linked to a promoter.

In another aspect, a targeting vector is provided wherein the targeting vector comprises a 5' homology arm homologous to a sequence present in a locus comprising a nucleotide sequence that is at least 90% identical to SEQ ID NO:1 or SEQ ID NO:4, a GOI, and a 3' homology arm homologous to a sequence present in a locus comprising a nucleotide sequence that is at least 90% identical to SEQ ID NO:1 or SEQ ID NO:4. In another embodiment, the targeting vector further comprises two, three, four, or five or more genes of interest.

In another aspect, a method is provided for modifying a CHO cell genome to integrate an exogenous nucleic acid sequence, comprising the step of introducing into the cell a vehicle that includes a vector, wherein the vector comprises an exogenous nucleic acid sequence wherein the exogenous nucleic acid integrates within a locus of the genome comprising a nucleotide sequence at least 90% identical to SEQ ID NO: 1 or SEQ ID NO: 4.

In some embodiments, the vector comprises a 5' homology arm homologous to a sequence present in a locus of the genome comprising a nucleotide sequence at least 90% identical to SEQ ID NO: 1 or SEQ ID NO: 4, an exogenous nucleic acid sequence, and a 3' homology arm homologous to a sequence present in a locus of the genome comprising a nucleotide sequence at least 90% identical to SEQ ID NO: 1 or SEQ ID NO: 4.

In some embodiments, the exogenous nucleic acid sequence in the vector comprises one or more recognition sequences. In other embodiments, the exogenous nucleic acid comprises one or more GOIs, such as a selectable marker or a nucleic acid encoding a POI. In still other embodiments, the exogenous nucleic acid comprises one or more GOIs and one or more recognition sequences.

In one embodiment, the vehicle comprises at least one additional vector or mRNA. In another embodiment, the additional vector is chosen from the group consisting of an adenovirus, a lentivirus, a retrovirus, an adeno-associated virus, an integrating phage vector, a non-viral vector, a transposon and/or transposase, an integrase substrate, and a plasmid. In some embodiments, the additional vector comprises a nucleotide sequence encoding a site-specific nuclease for integrating the exogenous nucleic acid sequence.

In certain embodiments, the site-specific nuclease comprises a zinc finger nuclease (ZFN), a ZFN dimer, a transcription activator-like effector nuclease (TALEN), a TAL effector domain fusion protein, or an RNA-guided DNA endonuclease.

In another aspect, a vehicle is provided for modifying a CHO cell genome to integrate an exogenous nucleic acid sequence, wherein the vehicle includes a vector, wherein the vector comprises a 5' homology arm homologous to a sequence present in a locus of the genome comprising a nucleotide sequence at least 90% identical to SEQ ID NO: 1 or SEQ ID NO: 4, an exogenous nucleic acid sequence, and a 3' homology arm homologous to a sequence present in a locus of the genome comprising a nucleotide sequence at least 90% identical to SEQ ID NO: 1 or SEQ ID NO: 4.

In some embodiments, the exogenous nucleic acid sequence comprises one or more recognition sequences. In other embodiments, the exogenous nucleic acid comprises one or more GOIs, such as a selectable marker or a nucleic acid encoding a POI. In still other embodiments, the exogenous nucleic acid comprises one or more GOIs and one or more recognition sequences.

In yet another aspect, a method is provided for modifying a CHO cell genome to express a therapeutic agent comprising a vehicle for introducing, into the genome, an exogenous nucleic acid comprising a sequence for expression of the therapeutic agent, wherein the vehicle comprises a 5' homology arm homologous to a sequence present in the nucleotide sequence of SEQ ID NO:1, a nucleic acid encoding the therapeutic agent, and a 3' homology arm homologous to a sequence present in the nucleotide sequence of SEQ ID NO:1 or SEQ ID NO:4.

In one more aspect, the invention provides a modified CHO host cell comprising a modified CHO genome wherein the CHO genome is modified by insertion of an exogenous recognition sequence within a locus of the genome having a nucleotide sequence at least 90% identical to SEQ ID NO: 1.

In another aspect, the invention provides a modified eukaryotic host cell comprising a modified eukaryotic genome wherein the eukaryotic genome is modified at a target integration site in a non-coding region of the genome to insert an exogenous nucleic acid. In some embodiments, the exogenous nucleic acid is a recognition sequence. In other embodiments, the host cell is a mammalian host cell, such as a CHO cell. In other embodiments, the target integration site comprises an expression-enhancing sequence such as SEQ ID NO:1, provided that the sequence does not code for any endogenous proteins. The invention also provides methods of making such a modified eukaryotic host cell.

In any of the aspects and embodiments described above, the expression-enhancing sequence can be placed in the indicated orientation as in SEQ ID NO:1, or in the reverse of the orientation of SEQ ID NO:1.

Any of the aspects and embodiments of the invention can be used in conjunction with any other aspect or embodiment of the invention, unless otherwise specified or apparent from the context.

Other objects and advantages will become apparent from a review of the ensuing detailed description.

BRIEF DESCRIPTION OF THE FIGURES

FIGS. 1A and 1B. FIG. 1A: Schematic diagram of an operable construct utilizing random introduction of a nucleic acid molecule expressing a GOI (for example, a multi-chain antibody) and multiple copies of a selection marker into a cell genome, for example a CHO genome for identifying a target locus. The exemplified construct includes: Heavy chain (HC); First copy selection marker, such as: hygromycin resistance gene (Hyg); First copy Light Chain (LC); Second copy selection marker (e.g. Hyg), Second copy Light Chain (LC); Third copy selection marker (e.g. Hyg). FIG. 1B: Example donor vector for integration via homologous recombination into the native locus identified as SEQ ID NO:1. 5' and 3' homology arms are derived from SEQ ID NO:1.

FIGS. 2A through 2C illustrate that the locus of SEQ ID NO: (LOCUS 1), operably linked to a gene of interest (GOI), exhibits enhanced mRNA expression of the GOI compared to the same GOI that is not operably linked to LOCUS 1, instead linked to a Control Locus. FIG. 2A: Equivalent number of gene copies exhibited for cells encoding an antibody gene of interest, i.e. one heavy chain (HC) and two light chains (LC) operably linked to the Control Locus vs. LOCUS 1. FIG. 2B: mRNA levels are higher for GOI expressed in LOCUS 1 compared to Control Locus mRNA. FIG. 2C: Protein titer is 3-fold higher for cells expressing the GOI in LOCUS 1 compared to protein titer produced from the cells expressing the same GOI in the Control Locus.

FIG. 4 shows a higher mRNA level of a gene of interest (GOI) as measured in a CHO cell pool expressing the GOI in LOCUS 1 (SEQ ID NO:1) compared to mRNA from a CHO cell pool expressing the same GOI, under the same regulatory conditions, but integrated within the control locus, i.e. EESYR.

DETAILED DESCRIPTION

Figure 3B:
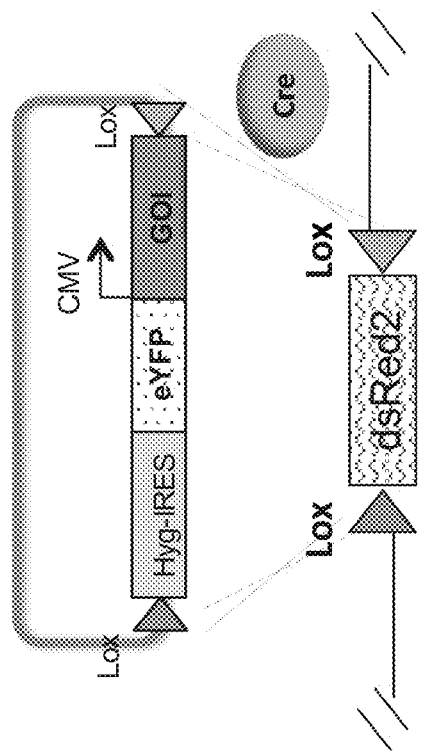
FIGS. 3A and 3B illustrate an example cassette comprising a fluorescent marker and a GOI integrated at LOCUS 1 (e.g. mKate flanked by lox sites to be exchanged with eYFP and a GOI) compared to the same cassette integrated at a Control Locus (exchanged with a different fluorescent marker, e.g. dsRed2, flanked by lox sites), wherein such integration employs Cre recombinase and recombinase-mediated cassette exchange (RMCE). Such cassettes were used in experiments to measure recombination efficiency and transcription of the GOI.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, or otherwise specified, all technical and scientific terms used herein have the same meaning as commonly understood by one of ordinary skill in the art to which this invention belongs.

Although any methods and materials similar or equivalent to those described herein can be used in the practice or testing of the present invention, particular methods and materials are now described. All publications mentioned herein are incorporated herein by reference in their entirety.

Definitions

DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. An expression-enhancing sequence of the locus of interest is operably linked to a gene of interest (GOI) where it is functionally related to the GOI, for example, where its presence results in enhanced expression and/or stable integration of the GOI.

The term "enhanced" when used to describe enhanced expression includes an enhancement of at least about 1.5-fold to at least about 3-fold enhancement in expression over what is typically observed by random integration of an exogenous sequence into a genome or by integration at a different locus, for example, as compared to a pool of random integrants of a single copy of the same expression construct. Fold-expression enhancement observed employing the sequences of the invention is in comparison to an expression level of the same gene, measured under substantially the same conditions, in the absence of a sequence of the invention, for example in comparison to integration at another locus into the same species genome. Enhanced recombination efficiency includes an enhancement of the ability of a locus to recombine (for example, employing recombinase-recognition sites). Enhancement refers to an efficiency of recombination over random recombination for example, without employing recombinase-recognition sites or the like, which is typically 0.1%. A preferred enhanced recombination efficiency is about 10-fold over random, or about 1%. Unless specified, the claimed invention is not limited to a specific recombination efficiency.

Where the phrase "exogenously added gene" or "exogenously added nucleic acid" is employed with reference to a locus of interest, the phrase refers to any DNA sequence or gene not present within the locus of interest as the locus is found in nature. For example, an "exogenously added gene" within a CHO locus (e.g., a locus comprising a sequence of SEQ ID NO:1), can be a hamster gene not found within the particular CHO locus in nature (i.e., a hamster gene from another locus in the hamster genome), a gene from any other species (e.g., a human gene), a chimeric gene (e.g., human/mouse), or any other gene not found in nature to exist within the CHO locus of interest.

Percent identity, when describing a locus of interest, such as SEQ ID NO:1 or SEQ ID NO:4, or a fragment thereof, is meant to include homologous sequences that display the recited identity along regions of contiguous homology, but the presence of gaps, deletions, or insertions that have no homolog in the compared sequence are not taken into account in calculating percent identity.

As used herein, a "percent identity" determination between, e.g., SEQ ID NO:1, or fragment thereof, with a species homolog would not include a comparison of sequences where the species homolog has no homologous sequence to compare in an alignment (i.e., SEQ ID NO:1 or the fragment thereof has an insertion at that point, or the species homolog has a gap or deletion, as the case may be). Thus, "percent identity" does not include penalties for gaps, deletions, and insertions.

A "homologous sequence" in the context of nucleic acid sequences refers to a sequence that is substantially homologous to a reference nucleic acid sequence. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding nucleotides are identical over a relevant stretch of residues. In some embodiments, the relevant stretch is a complete (i.e., full) sequence.

"Targeted insertion" refers to gene targeting methods employed to direct insertion or integration of the gene or nucleic acid sequence to a specific location on the genome, i.e., to direct the DNA to a specific site between two nucleotides in a contiguous polynucleotide chain. Targeted insertion may also be done for a particular gene cassette, which includes multiple genes, regulatory elements, and/or nucleic acid sequences. "Insertion" and "integration" are used interchangeably. It is understood that insertion of a gene or nucleic acid sequence (for example a nucleic acid sequence comprising an expression cassette) may result in (or may be engineered for) the replacement or deletion of one or more nucleic acids depending on the gene editing technique being utilized.

"Recognition site" or "recognition sequence" is a specific DNA sequence recognized by a nuclease or other enzyme to bind and direct site-specific cleavage of the DNA backbone. Endonucleases cleave DNA within a DNA molecule. Recognition sites are also referred to in the art as recognition target sites.

"Recombinase recognition site" is the specific DNA sequence recognized by a recombinase, such as Cre recombinase (Cre) or flippase (flp). Site-specific recombinases can perform DNA rearrangements, including deletions, inversions and translocations when one or more of their target recognition sequences are placed strategically into the genome of an organism. In one example, Cre specifically mediates recombination events at its DNA target recognition site loxP, which is composed of two 13-bp inverted repeats separated by an 8-bp spacer. More than one recombinase recognition site may be employed, for example, to facilitate a recombination-mediated exchange of DNA. Variants or mutants of recombinase recognition sites, for example lox sites, may also be employed (Araki, N. et al, 2002, *Nucleic Acids Research*, 30:19, e103).

"Recombinase-mediated cassette exchange" relates to a process for precisely replacing a genomic target cassette with a donor cassette. The molecular compositions typically provided in order to perform this process include 1) a genomic target cassette flanked both 5' and 3' by recognition target sites specific to a particular recombinase, 2) a donor cassette flanked by matching recognition target sites, and 3) the site-specific recombinase. Recombinase proteins are well known in the art (Turan, S. and Bode J., 2011. FASEB J., 25, pp. 4088-4107) and enable precise cleavage of DNA within a specific recognition target site (sequence of DNA) without gain or loss of nucleotides. Common recombinase/ site combinations include, but are not limited to, Cre/ox and Flp/frt.

A "vehicle" is a composition consisting of any polynucleotide or set of polynucleotides carrying an exogenous nucleic acid for introduction into a cell. A vehicle includes vectors, plasmids and mRNA molecules that are delivered to the cell by well-known transfection methods. In one example, an mRNA introduced into the cells may be transient and does not integrate into the genome, however the mRNA may carry exogenous nucleic acid necessary for the integration process to take place.

GENERAL DESCRIPTION

The invention is based at least in part on the discovery of unique sequences, i.e. loci, in a genome that exhibit more efficient recombination, insert stability, and higher level expression than other regions or sequences in the genome. The invention is also based at least in part on the finding that when such expression-enhancing sequences are identified, a suitable gene or construct can be exogenously added in or near the sequences and that the exogenously added gene can be advantageously expressed or utilized for further genomic modifications. Such sequences, termed expression-enhancing sequences are considered stable and are not located within a coding region of the genome. These expression-enhancing and stability regions can be engineered for future cloning or genome editing events. Thus, a reliable expression system is built into the genomic backbone of the cell.

The invention is also based on the specific targeting of an exogenous gene to the integration site. The methods of the invention allow efficient "conversion" of the cell genome into a useful cloning cassette, for example, by employing recombinase-mediated cassette exchange (RMCE). To this end, the methods of the invention employ cellular genome recombinase recognition sites for the placement of genes of interest to create highly productive cell lines for recombinant protein production.

The compositions of the invention can also be included in expression constructs for example, in expression vectors for cloning and engineering new cell lines. Expression vectors comprising the polynucleotides of the invention can be used to express proteins transiently, or can be integrated into a genome by random or targeted recombination such as, for example, homologous recombination or recombination mediated by recombinases that recognize specific recombination sites (e.g., Cre-lox-mediated recombination). Expression vectors comprising the polynucleotides of the invention can also be used to assess efficacy of other DNA sequences, for example, cis-acting regulatory sequences.

Integration sites are typically identified by either random integration or analysis of retroviral integration events. The CHO integration site described in detail herein was identified by random integration of DNA encoding a multi-chain antibody and the expressed protein was found to exhibit enhanced expression.

The example multi-chain antibody comprising one heavy chain (HC) and two copies of a light chain (LC) were randomly integrated into the genome in an expression cassette containing alternating hygromycin resistance genes (see, e.g. three identical Hyg genes as depicted in FIG. 1A). One stable and high expression clone resulted from the integration of the expression cassette within the loci identified as SEQ ID NO:1.

Compared to integration into another region of the CHO genome (control integration site), the example multi-chain antibody exhibits higher expression levels when integrated within the locus of SEQ ID NO:1. Interestingly, gene copy number is comparable for the antibody-expressing polynucleotides integrated within SEQ ID NO: versus the control integration site, however protein titers are 3-fold higher for antibody-expressing polynucleotides integrated within SEQ ID NO:1.

Figure 3A:
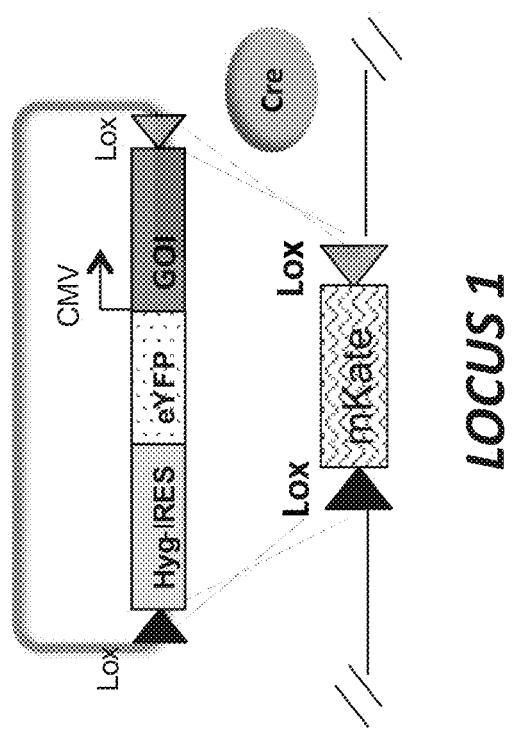

Targeted recombination methods were used to convert the CHO cell genome into a cloning construct containing recombinase recognition sites (see, e.g. FIGS. 3A-B).

Essentially, following identification of the integration site of SEQ ID NO:1, recombinase recognition sites (e.g., lox sites) were employed in the locus for introducing expression cassettes that comprise an expressible GOI, such as a selectable marker (see, e.g. FIGS. 3A-B), along with any other desirable elements such as, e.g., promoters, enhancers, markers, operators, ribosome binding sites (e.g. internal ribosome entry sites), etc.

An illustration of an example donor construct used for targeted integration of lox sites within SEQ ID NO:1, is shown in FIG. 1B. The donor construct comprises an expression cassette driven by a neomycin (neo) resistance gene and an internal ribosome entry site (IRES), wherein the cassette comprises a fluorescent marker (mKate) and is flanked on the 5' and 3' ends with recombinase recognition sites and 5' and 3' homology arms (homologous to SEQ ID NO:1). Insertion within the locus of SEQ ID NO: is shown, wherein the insertion results in the donor neo/mKate construct replacing the expression cassette comprising the hygromycin resistance marker, wherein the expression cassette within the SEQ ID NO:1 locus is flanked on its 5' and 3' ends by recombinase recognition sites connected to 5' and 3' homology arms (homologous to SEQ ID NO:1) (see FIG. 1B).

Compositions and methods are provided for stably integrating a nucleic acid sequence into a eukaryotic cell, wherein the nucleic acid sequence is capable of enhanced expression by virtue of being integrated in SEQ ID NO:1 or an expression-enhancing fragment thereof. Cells are provided that contain a recombinase recognition sequence within SEQ ID NO:1 convenient for inserting a GOI, in order to achieve expression of a protein of interest from the GOI. Compositions and methods are also provided for targeting the integration sites in connection with expression constructs, for example, expression vectors, and for adding an exogenous nucleic acid(s) into a CHO cell of interest.

Physical and Functional Characterization of a CHO Integration Site

The nucleic acid sequence of SEQ ID NO:1 (and broader nucleic acid sequence of SEQ ID NO:4) was empirically identified by sequences upstream and downstream of the integration site of a nucleic acid construct (comprising an expression cassette) of a cell line expressing a protein at a high level. The nucleic acid sequences of the invention provide sequences with a new functionality associated with enhanced expression and stability of a nucleic acid (for example, an exogenous nucleic acid comprising a GOI) and without being bound by any one theory, may function the same or differently from that previously described for cis-acting elements such as promoters, enhancers, locus control regions, scaffold attachment regions or matrix attachment regions. SEQ ID NO:1 does not appear to have any open reading frames (ORFs), making it unlikely that the locus encodes novel trans-activator proteins. A putative Zinc finger protein has been identified in the genomic locus 3' (downstream) of SEQ ID NO:4.

Expression-enhancing activity was identified with respect to integration of an expression cassette comprising a first hygromycin (Hyg) gene, a first GOI, a second Hyg gene, a second GOI, a third Hyg gene and a third GOI encoding sequence within a unique site of a non-coding region of CHO genomic DNA. Expression vectors comprising, for example, a 5' isolated 1 kb region and a 3' isolated 1 kb region identified from the non-coding region of CHO genomic DNA with respect to an expression cassette expressing a GOI were able to confer upon CHO cells transfected with them high levels of expression of recombinant proteins.

The invention encompasses expression vectors comprising reverse orientated SEQ ID NO:1 fragments or SEQ ID NO:4 fragments. Other combinations of the fragments described herein can also be developed. Examples of other combinations of the fragments described herein that can also be developed include sequences that include multiple copies of the expression-enhancing sequences disclosed herein, or sequences derived by combining the disclosed SEQ ID NO:1 fragments or SEQ ID NO:4 fragments with other nucleotide sequences to achieve optimal combinations of regulatory elements. Such combinations can be contiguously linked or arranged to provide optimal spacing of the SEQ ID NO:1 or SEQ ID NO:4 fragments (e.g., by the introduction of spacer nucleotides between the fragments). Regulatory elements can also be arranged to provide optimal spacing of a SEQ ID NO:1 fragment with respect to the regulatory elements.

SEQ ID NO:1 and SEQ ID NO: 4 disclosed herein were isolated from CHO cells. Other mammalian species (such as, for example, humans or mice), were found to have limited homology to the identified expression-enhancing region, however homologous sequences may be found in cell lines derived from other tissue types of *Cricetulus griseus*, or other homologous species, and can be isolated by techniques that are well-known in the art. For example, one may identify other homologous sequences by cross-species hybridization or PCR-based techniques. In addition, changes can be made in the nucleotide sequence set forth in SEQ ID NO:1, SEQ ID NO: 4, or fragments thereof, by site-directed or random mutagenesis techniques that are well known in the art. The resulting sequence variants can then be tested for expression-enhancing activity as described herein. DNAs that are at least about 90% identical in nucleic acid identity to SEQ ID NO:1, SEQ ID NO: 4, or fragments thereof, having expression-enhancing activity are isolatable by routine experimentation, and are expected to exhibit expression-enhancing activity. For fragments of SEQ ID NO:1 or SEQ ID NO: 4, percent identity refers to that portion of the reference native sequence that is found in the SEQ ID NO:1 fragment or SEQ ID NO: 4 fragment. Accordingly, homologs of SEQ ID NO:1, SEQ ID NO: 4, or fragments thereof, and variants thereof, are also encompassed by embodiments of the invention.

In certain embodiments, the fragment of SEQ ID NO:1 is selected from the group consisting of nucleotides spanning positions numbered 10-4,000; 100-3,900; 200-3,800; 300-3,700; 400-3,600; 500-3,500; 600-3,400; 700-3,300; 800-3,200; 900-3,100; 1,000-3,000; 1,100-2,900; 1,200-2,800; 1,300-2,700; 1,200-2,600; 1,300-2,500; 1,400-2,400; 1,500-2,300; 1,600-2,200; 1,700-2100; 1,800-2050; 1850-2050, 1,900-2040; 1950-2,025, 1990-2021, 2002-2021 and 2,010-2,015 of SEQ ID NO:1. In another embodiment, the fragment of SEQ ID NO:1 is selected from the group consisting of nucleotides spanning positions numbered 10-500; 500-1,000; 500-2,100; 1,000-1,500; 1,000-2,100; 1,500-2,000; 1,500-2,500; 2,000-2,500; 2,500-3,000; 2,500-3,500; 3,000-3,500; 3,000-4,000; and 3,500-4,000 of SEQ ID NO:1. In certain embodiments, the exogenous nucleic acid sequence integrates at or near specific sites within the fragment described above.

In another embodiment, the exogenous nucleic acid sequence is positioned within SEQ ID NO:1 or fragments thereof as described above, or within a sequence that is at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the expression-enhancing sequence of SEQ ID NO:1 or an expression-enhancing fragment thereof.

Cell populations expressing enhanced levels of a protein of interest can be developed using the methods provided herein. The absolute level of expression will vary with the specific protein, depending on how efficiently the protein is processed by the cell. Cell pools developed with exogenous sequence(s) integrated within the expression-enhancing sequences of the invention are stable over time, and can be treated as stable cell lines for most purposes. Recombination steps can also be delayed until later in the process of development of the cell lines of the invention.

CHO Expression-Enhancing Locus and Fragments Thereof

The invention encompasses an expression-enhancing fragment of a nucleotide sequence that is at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the nucleotide sequence of SEQ ID NO:1 or SEQ ID NO: 4. The invention includes vectors comprising a fragment, including for transient or stable transfection, spanning positions numbered 10-4,000; 100-3,900; 200-3,800; 300-3,700; 400-3,600; 500-3,500; 600-3.400; 700-3,300; 800-3,200; 900-3,100; 1,000-3,000; 1,100-2,900; 1,200-2,800; 1,300-2,700; 1,200-2.600; 1,300-2.500; 1,400-2.400; 1,500-2.300; 1,600-2,200; 1,700-2100; 1,800-2050; 1850-2050, 1,900-2040; 1950-2, 025, 1990-2021, 2002-2021 and 2,010-2,015 of SEQ ID NO:1. The invention also includes a eukaryotic cell comprising such a fragment wherein the fragment is exogenous to the cell and is integrated into the cell genome, and cells comprising such a fragment having at least one recombinase recognition site that is within, immediately 5', or immediately 3' to the fragment.

In one embodiment, the expression-enhancing fragment of SEQ ID NO:1 is located at a position within SEQ ID NO:1 spanning positions numbered 10-500; 500-1,000; 500-2,100; 1,000-1,500; 1,000-2,100; 1,500-2,000; 1,500-2.500; 2,000-2.500; 2,500-3.000; 2,500-3.500; 3,000-3,500; 3,000-4,000; or 3,500-4,000 of SEQ ID NO:1.

Where stable integration and/or enhanced transcription of an integrated polynucleotide is supported, the exact location of the locus insertion (i.e. integration) site with respect to the exemplified sites is not essential. Rather, the integration site can be at any position that is within or adjacent to SEQ ID NO:1 or a fragment of SEQ ID NO:1, or SEQ ID NO: 4 or a fragment of SEQ ID NO: 4, as described herein. Whether a specific chromosomal location within or adjacent to the locus of interest supports stable integration and efficient transcription of an integrated exogenous gene can be determined in accordance with standard procedures well known in the art or methods exemplified herein.

The integration sites considered herein are located within a locus comprising the nucleotide sequence of SEQ ID NO:1 or SEQ ID NO:4, or within close proximity to the locus of interest, e.g., less than about 1 kb, 500 base pairs (bp), 250 bp, 100 bp, 50 bp, 25 bp, 10 bp, or less than about 5 bp upstream (5') or downstream (3') with respect to the location of SEQ ID NO:1 on the chromosomal DNA. In still some other embodiments, the employed integration site is located at about 1000, 2500, 5000 or more base pairs upstream (5') or downstream (3') with respect to the location of SEQ ID NO:1 or SEQ ID NO:4 on the chromosomal DNA.

It is understood in the art that large genomic regions, such as scaffold/matrix attachment regions, are employed for efficient replication and transcription of chromosomal DNA. A scaffold/matrix attachment region (S/MAR), also known as called scaffold-attachment region (SAR), or matrix-associated or matrix attachment region (MAR), is a eukaryotic genomic DNA region where the nuclear matrix attaches. Without being bound by any one theory, S/MARs typically map to non-coding regions, separate a given transcriptional region (e.g. chromatin domain) from its neighbors, and also provide platforms for the machinery and/or binding of factors that enable transcription, such as recognition sites for DNAses or polymerases. Some S/MARs have been characterized at about 14-20 kb in length (Klar, et al. 2005, *Gene* 364:79-89). As such, integration of genes at LOCUS 1 (within or near SEQ ID NO:1 or SEQ ID NO:4) is expected to confer enhanced expression.

Those in the art will recognize that several elements may be optimized for high transcriptional activity at the subject locus, resulting in high expression of an inserted gene encoding a protein of interest. Elements to consider include a strong promoter to drive transcription, adequate transcriptional machinery, and DNA having an open and accessible configuration. Insertion at the subject locus may be optimized within the skill of the person in the art by targeting an integration site selected within SEQ ID NO:1 or SEQ ID NO:4.

In one embodiment, the expression-enhancing sequence of SEQ ID NO:1 is employed to enhance the expression of a GOI. FIG. 2A shows results of a GOI operably linked to SEQ ID NO:1 (LOCUS 1) compared to the same GOI integrated in a different locus in the CHO cell genome (Control Locus), The gene copy number measured for each cell line is equivalent, yet experiments show that the mRNA level and the protein titer of cells expressing the GOI are 3-fold higher for GOI operably linked to LOCUS 1.

In various embodiments, expression of a GOI can be enhanced by placing the GOI within SEQ ID NO:1 or SEQ ID NO: 4. In various embodiments, enhancement in expression is at least about 1.5-fold to about 3-fold or more.

Genetically Modifying the Target Locus

Methods for genetically engineering a cell genome in a particular location (i.e. target locus) may be achieved in several ways. Genetic editing techniques were used to stably integrate a nucleic acid sequence into a eukaryotic cell, wherein the nucleic acid sequence is an exogenous sequence not normally found in such cells. Clonal expansion is necessary to ensure that the cell progeny will share the identical genotypic and phenotypic characteristics of the engineered cell line. In some examples, native cells are modified by a homologous recombination technique to integrate an exogenous nucleic acid sequence within SEQ ID NO:1 or SEQ ID NO: 4. In other examples, cells are provided that contain at least one recombinase recognition sequence within SEQ ID NO:1 or SEQ ID NO: 4 convenient for integrating an exogenous nucleic acid sequence or a gene of interest.

In some examples, cells are provided that contain a first recombinase recognition sequence and a second recombinase recognition sequence wherein each of the first and the second recombinase recognition sequences is selected from the group comprising LoxP, Lox511, Lox5171, Lox2272, Lox2372, Loxm2, Lox-FAS, Lox71, Lox66 and the mutants thereof. In this case, where recombinase-mediated cassette exchange (RMCE) is desired, the site specific recombinase is Cre recombinase or its derivative. In other examples, each of the first and the second recombinase recognition sequences is selected from the group comprising FRT, F3, F5, FRT mutant-10, FRT mutant+10 and the mutants thereof, and in this scenario, where RCME is desired, the site-specific recombinase is Flp recombinase or its derivative. In yet another example, each of said first and the second recombinase recognition sequences is selected from the group comprising attB, attP and the mutants thereof, and in this case where RMCE is desired, the site-specific recombinase is phiC31 integrase or its derivative.

In one aspect, methods and compositions for stably integrating a nucleic acid sequence within SEQ ID NO:1 or SEQ ID NO: 4, or an expression-enhancing fragment thereof, are via homologous recombination. A nucleic acid molecule, .i.e. gene or polynucleotide of interest, can be inserted into the targeted locus (i.e. SEQ ID NO:1) by homologous recombination or by using site-specific nuclease methods that specifically target sequences at the integration sites. For homologous recombination, homologous polynucleotide molecules (i.e. homologous arms) line up and exchange a stretch of their sequences. A transgene can be introduced during this exchange if the transgene is flanked by homologous genomic sequences. In one example, a recombinase recognition site can be introduced into the host cell genome at the integration sites.

Homologous recombination in eukaryotic cells can be facilitated by introducing a break in the chromosomal DNA at the integration site. Model systems have demonstrated that the frequency of homologous recombination during gene targeting increases if a double-strand break is introduced within the chromosomal target sequence. This may be accomplished by targeting certain nucleases to the specific site of integration. DNA-binding proteins that recognize DNA sequences at the target locus are known in the art. Gene targeting vectors are also employed to facilitate homologous recombination. In the absence of a gene targeting vector for homology directed repair, the cells frequently close the double-strand break by non-homologous end-joining (NHEJ) which may lead to deletion or insertion of multiple nucleotides at the cleavage site. Should insertions or deletions (InDels) occur, as such, a small number of nucleotides are either inserted or deleted at random at the site of the break and these InDels may shift or disrupt any open reading frame (ORF) of a gene within the target locus. It is understood that the locus identified as SEQ ID NO:1 (or SEQ ID NO:4) is not a gene coding region. Hence, no disruption of endogenous gene transcription is envisioned by insertion and/or deletion at this locus.

Homology directed repair (or homology directed recombination) (HDR) is particularly useful for inserting or integrating genes at the subject locus. A donor construct comprises homologous arms derived from SEQ ID NO:1 or SEQ ID NO:4 as described herein.

Gene targeting vector construction and nuclease selection are within the skill of the artisan to whom this invention pertains.

In some examples, zinc finger nucleases (ZFNs), which have a modular structure and contain individual zinc finger domains, recognize a particular 3-nucleotide sequence in the target sequence (e.g. site of targeted integration). Some embodiments can utilize ZFNs with a combination of individual zinc finger domains targeting multiple target sequences.

Transcription activator-like (TAL) effector nucleases (TALENs) may also be employed for site-specific genome editing. TAL effector protein DNA-binding domain is typically utilized in combination with a non-specific cleavage domain of a restriction nuclease, such as FokI. In some embodiments, a fusion protein comprising a TAL effector protein DNA-binding domain and a restriction nuclease cleavage domain is employed to recognize and cleave DNA at a target sequence within the locus of the invention (Boch J et al., 2009 *Science* 326:1509-1512).

RNA-guided endonucleases (RGENs) are programmable genome engineering tools that were developed from bacterial adaptive immune machinery. In this system—the clustered regularly interspaced short palindromic repeats (CRISPR)/CRISPR-associated (Cas) immune response—the protein Cas9 forms a sequence-specific endonuclease when complexed with two RNAs, one of which guides target selection. RGENs consist of components (Cas9 and tracrRNA) and a target-specific CRISPR RNA (crRNA). Both the efficiency of DNA target cleavage and the location of the cleavage sites vary based on the position of a protospacer adjacent motif (PAM), an additional requirement for target recognition (Chen, H. et al, *J. Biol. Chem.* published online Mar. 14, 2014, as Manuscript M113.539726).

Strategies for identifying sequences unique for the specific targeting locus of SEQ ID NO:1 are known in the art, however, alignment of many of these sequences to the CHO genome reveals potential off-target sites with 16-17 base pair match. One example 20 bp Guide RNA encoded by the sequence set forth in SEQ ID NO:5 (corresponding to nucleotides 1990-2001 of SEQ ID NO: 1) is useful for RNA-guided CRISPR/Cas gene editing of SEQ ID NO:1 or SEQ ID NO:4. A plasmid comprising a promoter that drives expression of the small guided RNA and a tracrRNA (for ex. SEQ ID NO:6), as well as carrying a suitable Cas9 enzyme under control of a promoter may be co-transfected with a donor vector (carrying the gene of interest flanked by 5' and 3' homology arms) to employ targeted integration by this method. Various modifications and variants of the RNA molecules in addition to those described hereinabove are apparent to those skilled in the art and are intended to fall within the scope of the invention.

In some embodiments, the vehicle for introducing, into the genome, an exogenous nucleic acid comprising a sequence coding for the gene of interest or recognition sequence or gene cassette, as the case may be, comprises a vector carrying the exogenous nucleic acid and one or more additional vectors or mRNA. In one embodiment, the one or more additional vectors or mRNA comprise a nucleotide sequence encoding a site-specific nuclease, including but not limited to a zinc finger nuclease (ZFN), a ZFN dimer, a transcription activator-like effector nuclease (TALEN), a TAL effector domain fusion protein, and an RNA-guided DNA endonuclease. In certain embodiments, the one or more vectors or mRNA comprise a first vector comprising a guide RNA, a tracrRNA and a nucleotide sequence encoding a Cas enzyme, and a second vector comprising a donor (exogenous) nucleotide sequence. Such donor sequence comprises a nucleotide sequence coding for the gene of interest, or the recognition sequence, or the gene cassette comprising any one of these exogenous elements intended for targeted insertion. Where mRNA is used, the mRNA can be transfected into the cell by means of common transfection methods known to the skilled person and may encode an enzyme, for example a transposase or endonuclease. Although an mRNA introduced into the cells may be transient and does not integrate into the genome, the mRNA may carry an exogenous nucleic acid necessary or beneficial for the integration to take place. In some instances, mRNA is chosen in order to eliminate any risk of long-lasting side effects of an accessory polynucleotide, where only short-term expression is required to achieve the desired integration of a GOI.

Still other methods of homologous recombination are available to the skilled artisan, such as BuD-derived nucleases (BuDNs) with precise DNA-binding specificities (Stella, S. et al. *Acta Cryst.* 2014, D70, 2042-2052). Precise genome modification methods are chosen based on the tools available compatible with unique target sequences within SEQ ID NO:1 so that disruption of the cell phenotype is avoided.

Gene Targeting Constructs

The polynucleotide sequence to be integrated into the host genome may be any industrially useful DNA sequence, such as a recognition sequence, for the generation of cellular expression systems. The polynucleotide sequence to be integrated into the host genome may encode any therapeutically or industrially useful protein or proteins as described herein. Identifying the target sequence within the target locus to integrate the exogenous nucleic acid sequence depends on a number of factors. Depending on the method of homologous recombination utilized, it is well within the skill of the artisan to select sequences homologous to SEQ ID NO:1 or SEQ ID NO: 4. Site-specific nuclease vectors, when employed, require additional components (sequence compositions) that recognize the specific site intended for DNA cleavage.

As such, a gene targeting construct typically incorporates such nucleotide sequences that facilitate the targeted integration of an exogenous nucleic acid sequence into the locus of interest. In some embodiments, the construct comprises a first homologous arm and a second homologous arm. In other embodiments, the construct (e.g. a gene cassette) comprises homologous arms derived from SEQ ID NO:1 or SEQ ID NO:4. In some embodiments, the homology arms comprise a nucleotide sequence homologous to a nucleotide sequence present in SEQ ID NO:1 or SEQ ID NO:4. In specific embodiments, the construct comprises a 5' homology arm having the nucleotide sequence of SEQ ID NO: 2 (corresponding to nucleotides 1001-2001 of SEQ ID NO: 1), and a 3' homology arm having the nucleotide sequence of SEQ ID NO:3 (corresponding to nucleotides 2022-2001 of SEQ ID NO: 1). Homologous arms, for example a first homologous arm (also called 5' homology arm) and a second homologous arm (also called 3' homology arm) are homologous to a targeted sequence within the locus. The homologous arms from 5' to 3' may expand a region or targeted sequence within the locus that comprises at least 1 kb, or at least about 2 kb, or at least about 3 kb, or at least about 4 kb, or at least 5 kb, or at least about 10 kb. In other embodiments, the total number of nucleotides of a targeted sequence selected for a first and second homologous arm comprises at least 1 kb, or at least about 2 kb, or at least about 3 kb, or at least about 4 kb, or at least 5 kb, or at least about 10 kb. In some instances, the distance between the 5' homology arm and the 3' homology arm (homologous to the targeted sequence) comprises at least 5 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, or at least 1 kb, or at least about 2 kb, or at least about 3 kb, or at least about 4 kb, or at least 5 kb, or at least about 10 kb. In instances where SEQ ID NO: 2 and SEQ ID NO: 3 are chosen as 5' and 3' homology arms, the distance between the two homology arms can be 20 nucleotides (corresponding to nucleotides 2002-2021 of SEQ ID NO: 1); and such homology arms can mediate integration of an exogenous nucleic acid sequence within a locus comprising SEQ ID NO: 1, e.g., within nucleotides 1990-2021 or 2002-2021 of SEQ ID NO: 1, and a simultaneous deletion of nucleotides 2002-2021 of SEQ ID NO: 1.

In other embodiments, the construct comprises a first homologous arm and a second homologous arm, wherein the first and second homologous arms combined comprise a targeted sequence which replaces an endogenous sequence within the locus. In yet other embodiments, the first and second homologous arms comprise a targeted sequence which integrates or inserts within an endogenous sequence within the locus.

Modified cell lines were created by integrating one or more recombinase recognition sites at a location within SEQ ID NO:1. These modified cell lines may also include additional exogenous genes for negative or positive selection of the expressed gene of interest.

The invention provides methods for modifying a CHO cell genome comprising introducing one or more vehicles into the cell, wherein the one or more vehicles comprise an exogenous nucleic acid comprising a sequence for integration, a 5' homology arm homologous to a sequence present in the nucleotide sequence of SEQ ID NO:1, and a 3' homology arm homologous to a sequence present in the nucleotide sequence of SEQ ID NO:1. In some embodiments, the methods further provide one or more vehicles comprising a nuclease and compositions for site-specific DNA cleavage at the integration site.

The modified cell lines may be utilized as convenient and stable expression systems for recombinase-mediated cassette exchange (RMCE). A nucleic acid sequence encoding a protein of interest can be conveniently integrated into the modified cell comprising SEQ ID NO:1 or an expression-enhancing fragment thereof, having at least one recombinase recognition site, for example, through an RMCE process.

Recombinant expression vectors can comprise synthetic or cDNA-derived DNA fragments encoding a protein, operably linked to a suitable transcriptional and/or translational regulatory element derived from mammalian, viral or insect genes. Such regulatory elements include transcriptional promoters, enhancers, sequences encoding suitable mRNA ribosomal binding sites, and sequences that control the termination of transcription and translation, as described in detail below. Mammalian expression vectors can also comprise nontranscribed elements such as an origin of replication, other 5' or 3' flanking nontranscribed sequences, and 5' or 3' nontranslated sequences such as splice donor and acceptor sites. A selectable marker gene to facilitate recognition of transfectants may also be incorporated.

Fluorescent markers are suitable selectable marker genes for the recognition of gene cassettes that have or have not been successfully inserted and/or replaced, as the case may be. Examples of fluorescent markers are well-known in the art, including, but not limited to Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein (e.g. mKate, mKate2, mPlum, mRaspberry or E2-crimson. See also, e.g., Nagai, T., et al. 2002 *Nature Biotechnology* 20:87-90; Heim, R. et al. 23 Feb. 1995 *Nature* 373:663-664; and Strack, R. L. et al. 2009 *Biochemistry* 48:8279-81.

Transcriptional and translational control sequences in expression vectors useful for transfecting vertebrate cells may be provided by viral sources. For example, commonly used promoters and enhancers are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the recombinant protein is to be expressed.

DNA sequences derived from the SV40 viral genome, for example, the SV40 origin, early and late promoter, enhancer, splice, and polyadenylation sites may be used to provide other genetic elements useful for expression of a heterologous DNA sequence. Early and late promoters are particularly useful because both are obtained easily from the SV40 virus as a fragment that also comprises the SV40 viral origin of replication (Fiers et al., Nature 273:113, 1978). Smaller or larger SV40 fragments may also be used. Typically, the approximately 250 bp sequence extending from the Hind III site toward the BglI site located in the SV40 origin of replication is included.

Bicistronic expression vectors used for the expression of multiple transcripts have been described previously (Kim S. K. and Wold B. J., Cell 42:129, 1985) and can be used in combination with an expression-enhancing sequence of the invention, e.g. SEQ ID NO:1, or a fragment thereof. Other types of expression vectors will also be useful, for example, those described in U.S. Pat. No. 4,634,665 (Axel et al.) and U.S. Pat. No. 4,656,134 (Ringold et al.).

Proteins of Interest

Any protein of interest suitable for expression in eukaryotic cells can be used. For example, the protein of interest includes, but is not limited to, an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins of interest may be simple polypeptides consisting of a single subunit, or complex multisubunit proteins comprising two or more subunits.

Host Cells and Transfection

The host cells used in the methods of the invention are mammalian host cells including, for example, Chinese hamster ovary (CHO) cells and mouse cells. In a preferred embodiment, the invention provides a nucleic acid sequence fragment of SEQ ID NO:1 that encodes an expression-enhancing sequence in a CHO cell. An integration site can be found within SEQ ID NO:1, or any fragment of SEQ ID NO:1. An integration site, for example, may be a recombinase recognition site placed within SEQ ID NO:1, or any fragment of SEQ ID NO:1. One example of a suitable integration site is a LoxP site. Another example of a suitable integration site is two recombinase recognition sites, for example, selected from the group consisting of a LoxP site, a Lox511 site, a Lox2272 site, a Lox2372 site, a Loxm2 site, a Lox71 site, a Lox66 site and a Lox5171 site. In other embodiments, the integration site is located at a position within a sequence or adjacent to a position within a sequence selected from the group consisting of nucleotides spanning positions numbered 10-4,000; 100-3,900; 200-3,800; 300-3,700; 400-3,600; 500-3,500; 600-3,400; 700-3,300; 800-3, 200; 900-3,100; 1,000-3,000; 1,100-2,900; 1,200-2,800; 1,300-2,700; 1,200-2,600; 1,300-2,500; 1,400-2,400; 1,500-2,300; 1,600-2,200; 1,700-2100; 1,800-2050; 1850-2050, 1,900-2040; 1950-2,025, 1990-2021, 2002-2021 and 2,010-2,015 of SEQ ID NO:1. In certain embodiments, the integration site at a position within SEQ ID NO:1 or adjacent to a position within SEQ ID NO:1 is selected from the group consisting of nucleotides spanning positions numbered 1990-1991, 1991-1992, 1992-1993, 1993-1994, 1995-1996, 1996-1997, 1997-1998, 1999-2000, 2001-2002, 2002-2003, 2003-2004, 2004-2005, 2005-2006, 2006-2007, 2007-2008, 2008-2009, 2009-2010, 2010-2011, 2011-2012, 2012-2013, 2013-2014, 2014-2015, 2015-2016, 2016-2017, 2017-2018, 2018-2019, 2019-2020, and 2020-2021 of SEQ ID NO:1.

The invention includes a mammalian host cell transfected with an expression vector or an mRNA of the invention. While any mammalian cell may be used, in one particular embodiment the host cell is a CHO cell.

Transfected host cells include cells that have been transfected with expression vectors or mRNA molecules that comprise a sequence encoding a protein or polypeptide. Expressed proteins may be secreted into the culture medium, depending on the nucleic acid sequence selected, but may be retained in the cell or deposited in the cell membrane. Various mammalian cell culture systems can be employed to express recombinant proteins. Other cell lines developed for specific selection or amplification schemes will also be useful with the methods and compositions provided herein, provided that a target locus having at least 80% homology to SEQ ID NO:1 has been identified. An embodied cell line is the CHO cell line designated K1. To achieve high volume production of recombinant proteins, the host cell line may be pre-adapted to bioreactor medium in the appropriate case.

Several transfection protocols are known in the art, and are reviewed in Kaufman (1988) Meth. Enzymology 185: 537. The transfection protocol chosen will depend on the host cell type and the nature of the GOI, and can be chosen based upon routine experimentation. The basic requirements of any such protocol are first to introduce DNA encoding the protein of interest into a suitable host cell, and then to identify and isolate host cells which have incorporated the heterologous DNA in a relatively stable, expressible manner. mRNA molecules encoding proteins useful for integration into the host cell genome or other function may be transient and therefore time-limited.

Transfection protocols as well as protocols for introducing polypeptides or polynucleotide sequences into cells may vary. Non-limiting transfection methods include chemical-based transfection methods include the use of liposomes; nanoparticles; calcium phosphate (Graham et al. (1973). *Virology* 52 (2): 456-67, Bacchetti et al. (1977) *Proc Natl Acad Sci USA* 74 (4): 1590-4 and, Kriegler, M (1991). Transfer and Expression: A Laboratory Manual. New York: W. H. Freeman and Company. pp. 96-97); dendrimers; or cationic polymers such as DEAE-dextran or poyethylenimine. Non chemical methods include electroporation; Sono-poration; and optical transfection. Particle-based transfection include the use of a gene gun, magnet assisted transfection (Bertram, J. (2006) *Current Pharmaceutical Biotechnology* 7, 277-28). Viral methods can also be used for transfection. mRNA delivery includes methods using TransMessenger™ and TransIT® (Bire et al. *BMC Biotechnology* 2013, 13:75).

One commonly used method of introducing heterologous DNA into a cell is calcium phosphate precipitation, for example, as described by Wigler et al. (Proc. Natl. Acad. Sci. USA 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., (1980) Proc. Natl. Acad. Sci. USA 77:2163) is another useful method of introducing heterologous DNA. Protoplast fusion protocols frequently yield multiple copies of the plasmid DNA integrated into the mammalian host cell genome, and this technique requires the selection and amplification marker to be on the same plasmid as the GOI.

Electroporation can also be used to introduce DNA directly into the cytoplasm of a host cell, for example, as described by Potter et al. (Proc. Natl. Acad. Sci. USA 81:7161, 1988) or Shigekawa et al. (BioTechniques 6:742, 1988). Unlike protoplast fusion, electroporation does not require the selection marker and the GOI to be on the same plasmid.

Other reagents useful for introducing heterologous DNA into a mammalian cell have been described, such as Lipofectin™ Reagent and Lipofectamine™ Reagent (Gibco BRL, Gaithersburg, Md.). Both of these commercially available reagents are used to form lipid-nucleic acid complexes (or liposomes) which, when applied to cultured cells, facilitate uptake of the nucleic acid into the cells.

In one embodiment, the introducing one or more of the polynucleotides into a cell is mediated by electroporation, by intracytoplasmic injection, by a viral infection, by an adenovirus, by lentivirus, by retrovirus, by transfection, by lipid-mediated transfection or is mediated via Nucleofection™.

A method for amplifying the GOI is also desirable for expression of the recombinant protein, and typically involves the use of a selection marker (reviewed in Kaufman supra). Resistance to cytotoxic drugs is the characteristic most frequently used as a selection marker, and can be the result of either a dominant trait (e.g., can be used independent of host cell type) or a recessive trait (e.g., useful in particular host cell types that are deficient in whatever activity is being selected for). Several amplifiable markers are suitable for use in the expression vectors of the invention (e.g., as described in Sambrook, Molecular Biology: A Laboratory Manual, Cold Spring Harbor Laboratory, N Y, 1989; pgs 16.9-16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytotoxic agents (e.g., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifiable (Kaufman, R. J., supra,). Several suitable selection systems exist for mammalian hosts (Sambrook supra, pgs 16.9-16.15). Co-transfection protocols employing two dominant selectable markers have also been described (Okayama and Berg, Mol. Cell Biol 5:1136,1985).

Useful regulatory elements, described previously or known in the art, can also be included in the nucleic acid constructs used to transfect mammalian cells. The transfection protocol chosen and the elements selected for use therein will depend on the type of host cell used. Those of skill in the art are aware of numerous different protocols and host cells, and can select an appropriate system for expression of a desired protein, based on the requirements of the cell culture system used.

Other features of the invention will become apparent in the course of the following descriptions of exemplary embodiments which are given for illustration of the invention and are not intended to be limiting thereof.

EXAMPLES

The following examples are put forth so as to provide those of ordinary skill in the art how to make and use the methods and compositions described herein, and are not intended to limit the scope of the invention. Efforts have been made to ensure accuracy with respect to numbers used (e.g., amount, temperature, etc.) but some experimental error and deviation should be accounted for. Unless indicated otherwise, parts are parts by weight, molecular weight is average molecular weight, temperature is in degrees Centigrade, and pressure is at or near atmospheric.

Example 1. Identification of Locus of Interest and Characterization of Integration Sites CHO K1 cells were transfected with two plasmids containing antibody sequences and selectable antibiotic resistance genes as selectable markers. Selection of stable transfectants was performed by expanding cells in the presence of antibiotics. Individual cell clones expressing high levels of antibodies were isolated with FASTR® sorting technology (see U.S. Pat. No. 8,673,589B2). Several clones exhibiting the highest antibody expression levels were identified.

The genomic DNA from these clones was fragmented with Covaris Adaptive Focused Acoustics (AFA)™ technology (Fisher, S. et al. 2011, *Genome Biology* 12:R1). DNA libraries were generated (Agilent SureSelectXT #G9612A) and incubated with custom-made biotinylated RNA baits (Agilent SureSelectXT #5190-4811) designed against the entire plasmid sequences that were introduced into CHO cells. Genomic DNA fragments that contain plasmid sequences were enriched with magnetic Streptavidin beads and subjected to Illumina MiSeq sequencing to identify the plasmid integration sites. Fusion sequences that contain both plasmid sequence and CHO genome sequence were analyzed and aligned to the CHO genome. A single integration site was confirmed by Southern blot analysis and PCR followed by sequencing. The integration site having the nucleotide sequence of SEQ ID NO:1 was identified as an expression hotspot (see also GenBank Locus ID No. AFTD01150902.1, nt35529:39558). The integration sites were analyzed to determine their suitability for further generation of cell lines. It was desirable that the integration sites are located in a non-coding region that does not disrupt the cell's normal genomic machinery, e.g. translation of proteins, or alter the cell's phenotype.

From Blat search (Kent W J., BLAT—the BLAST-like alignment tool. *Genome Res.* 2002 April; 12(4):656-64) alignment, SEQ ID NO:1 shares very low homology to mouse and human genome sequences. Sequence blast of SEQ ID NO:1 against CHO-1[ATCC]_refseq_transcript revealed that the identified locus sequence does not contain any coding regions for any known genes. The broader sequence of SED ID NO:4, which encompasses SEQ ID NO:1, was also identified as a locus suitable for targeted integration.

The integration site sequences were determined to be located in non-coding regions of the CHO and mouse genomes, and further utilized in the below described experiments.

Example 2. Exogenous DNA Efficiently Incorporated into Host Cell Integration Sites Targeted insertion of exogenous genes into the specific locus of the CHO genome identified as SEQ ID NO:1 was done by employing a TALE nuclease (TALEN). The construct containing antibody heavy and light chain sequences randomly integrated into the cell genome, as in Example 1, was targeted by TALEN. TALEN was targeted to locations within the three identical Hyg genes of the antibody expression construct (see FIG. 1A). The TALEN target cleavage site for the Hyg sequence was based on ZiFit.partners.org (ZiFit Targeter Version 4.2). TALENs were designed based on known methods (Boch J et al., 2009 Science 326:1509-1512).

A donor mKate vector (see FIG. 1B) and TALEN-encoding vector were transfected into the CHO host cells using standard Lipofectin protocol (LIPOFECTAMINE, Life Technologies, Gaithersburg, Md.). Cells were cultured and stable clones with desirable features were isolated and sorted by FACS. Single integration in the desired locus was confirmed by Southern blot and PCR.

Example 3. Targeted Recombination of the Engineered Cells at the Locus of Interest by RMCE A CHO cell line expressing high levels of a flourescent gene, e.g. mKate, wherein the gene is flanked by lox sites within the locus of interest, was selected for isolation. A second CHO cell line expressing a second flourescent gene, dsRed, wherein the gene is flanked by lox sites is located within a control locus, i.e. EESYR (U.S. Pat. No. 8,389, 239B2, issued Mar. 5, 2013).

Transfected CHO cells were adapted to grow in suspension in a serum-free production medium. The cells were then transfected in a ten centimeter plate with a donor expression vector and a plasmid encoding Cre recombinase. The donor expression vector contains a gene of interest encoding an Fc fusion protein flanked by Lox sites (see FIG. 3A or 3B). Cells were cultured in culture medium with 400 μg/ml hygromycin for two weeks after transfection, and cells expressing eYFP but not mKate (or dsRed in the case of EESYR locus integration) were isolated using flow cytometry. Cells expressing eYFP were expanded in suspension cultures in serum-free production medium, and mRNA levels were determined by qRT-PCR using standard procedures for each cell pool encoding the Fc fusion protein (see FIG. 4).

Recombination exchange efficiency (percent population of surviving cells expressing from the donor cassette marker, i.e. eYFP, as exchanged with the red marker, i.e. mKate or dsRed) was compared between cell pools (Table 1). High recombination exchange efficiency was observed at each locus.

TABLE 1

Recombination Efficiency

|  | Red marker | Exchange efficiency (%) (Red marker+/eYFP−) | Random Integration (%) (Red marker+/eYFP+) |
|---|---|---|---|
| LOCUS 1 (SEQ ID NO: 1) | mKate | 72 | 27 |
| Control Locus (EESYR) | dsRed | 92 | 7 |

Transcription was observed at a higher rate (1.5-fold higher) in the cell pool having an engineered LOCUS1 compared to the Control Locus (FIG. 4).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

---

We claim:

1. A cell comprising an exogenous nucleic acid integrated within a locus of the genome of the cell, wherein the locus comprises a nucleotide sequence that has a sequence identity of at least 98% to SEQ ID NO: 1 or SEQ ID NO: 4, and wherein the exogenous nucleic acid comprises a first selectable marker under control of a promoter, wherein the cell is a Chinese hamster ovary (CHO) cell.

2. The cell of claim 1, wherein the exogenous nucleic acid further comprises a second selectable marker under control of a promoter, and wherein the second selectable marker is different from the first selectable marker.

3. The cell of claim 2, wherein the exogenous nucleic acid further comprises a third selectable marker under control of a promoter, and wherein the third selectable marker is different from the first selectable marker and the second selectable marker.

4. The cell of claim 3, wherein the third selectable marker is a fluorescent protein gene.

5. The cell of claim 4, wherein the fluorescent protein gene is selected from the group consisting of Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein.

6. The cell of claim 2, wherein the second selectable marker is a fluorescent protein gene.

7. The cell of claim 6, wherein the fluorescent protein gene is selected from the group consisting of Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein.

8. The cell of claim 1, wherein the first selectable marker is a drug resistance gene.

9. The cell of claim 8, wherein the drug resistance gene is selected from the group consisting of a neomycin resistance gene, a hygromycin resistance gene, and a kanamycin resistance gene.

10. The cell according to claim 1, further comprising a gene of interest under control of a promoter.

11. A CHO cell comprising an exogenous nucleic acid integrated within a locus of the genome of the cell, wherein the locus comprises a nucleotide sequence that has a sequence identity of at least 98% to SEQ ID NO:1 or SEQ ID NO:4, and wherein the exogenous nucleic acid comprises,
(1) a first selectable marker under control of a promoter,
(2) a second selectable marker under control of a promoter,
wherein the first selectable marker is a drug resistance gene is selected from the group consisting of a neomycin resistance gene, a hygromycin resistance gene, and a kanamycin resistance gene, and the second selectable marker is fluorescent protein gene selected from the group consisting of Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein; and
(3) a gene of interest under control of a promoter.

12. The cell according to claim 11, further comprising a third selectable marker.

13. The cell according to claim 12, wherein the third selectable marker is a fluorescent protein gene selected from the group consisting of Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein.

14. The cell according to claim 12, wherein the cell comprises more than one gene of interest to be expressed.

15. A method of producing a protein of interest, wherein the method comprises the steps of:
A) providing a CHO cell comprising an exogenous nucleic acid integrated within a locus of the genome of the cell, wherein the locus comprises a nucleotide sequence that has a sequence identity of at least 98% to SEQ ID NO:1 or SEQ ID NO:4, and wherein the exogenous nucleic acid comprises
(1) a first selectable marker under control of a promoter;
(2) a second selectable marker under control of a promoter,
wherein the first selectable marker is a drug resistance gene is selected from the group consisting of a neomycin resistance gene, a hygromycin resistance gene, and a kanamycin resistance gene, and the second selectable marker is fluorescent protein gene selected from the group consisting of Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein; and
(3) a gene of interest under control of a promoter, wherein the gene of interest encodes the protein of interest; and B) culturing the cell under conditions that allow expression of the gene of interest thereby producing the protein of interest.

\* \* \* \* \*